(12) United States Patent
Park et al.

(10) Patent No.: US 9,657,345 B2
(45) Date of Patent: May 23, 2017

(54) POLYNUCLEOTIDE AND USE THEREOF

(71) Applicant: Samsung Electronics Co., Ltd., Suwon-si, Gyeonggi-do (KR)

(72) Inventors: Dong-hyun Park, Chuncheon-si (KR); Sung-woo Hong, Gwangmyeong-si (KR); Kyung-hee Park, Seoul (KR); Myo-yong Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 11 days.

(21) Appl. No.: 13/899,223

(22) Filed: May 21, 2013

(65) Prior Publication Data

US 2014/0141418 A1    May 22, 2014

(30) Foreign Application Priority Data

Nov. 19, 2012 (KR) .................. 10-2012-0131026

(51) Int. Cl.
*C12Q 1/68* (2006.01)
*C07H 21/00* (2006.01)
*C12P 19/34* (2006.01)

(52) U.S. Cl.
CPC ......... *C12Q 1/6876* (2013.01); *C12Q 1/6844* (2013.01)

(58) Field of Classification Search
CPC ........ C12Q 1/68; C12Q 1/686; C12Q 1/6883; C12Q 1/6844; A61K 38/00; C12N 15/10; C12P 19/34
USPC .................. 435/6.1; 536/22.1, 23.1, 24.3
See application file for complete search history.

(56) References Cited

U.S. PATENT DOCUMENTS

| | | | |
|---|---|---|---|
| 6,180,778 B1 | 1/2001 | Bastian et al. | |
| 7,575,863 B2 | 8/2009 | Chen et al. | |
| 7,897,356 B2 | 3/2011 | Klass et al. | |
| 8,021,847 B2 | 9/2011 | Pietrzkowski | |
| 2001/0039039 A1* | 11/2001 | Weissman et al. | 435/91.1 |
| 2002/0042059 A1* | 4/2002 | Makarov | C12Q 1/6855 435/6.1 |
| 2004/0171047 A1 | 9/2004 | Dahl et al. | |
| 2005/0079523 A1* | 4/2005 | Hafner et al. | 435/6 |
| 2005/0266418 A1 | 12/2005 | Chen et al. | |
| 2007/0128632 A1* | 6/2007 | Spier | C12Q 1/6858 435/6.12 |
| 2008/0131878 A1 | 6/2008 | Latham et al. | |
| 2009/0220969 A1 | 9/2009 | Chiang et al. | |
| 2010/0112644 A1 | 5/2010 | Kim et al. | |
| 2012/0071332 A1 | 3/2012 | Busk | |

FOREIGN PATENT DOCUMENTS

| | | |
|---|---|---|
| KR | 2011-66158 A | 6/2011 |
| KR | 2012-49776 A | 1/2013 |
| KR | 2012-51066 A | 1/2013 |
| KR | 2012-41601 A | 10/2013 |
| KR | 2012-49279 A | 12/2013 |
| KR | 2012-131026 A | 5/2014 |
| WO | WO 2006/108423 A2 | 10/2006 |
| WO | WO 2008/119072 A1 | 10/2008 |
| WO | WO 2010/120803 A2 | 10/2010 |
| WO | WO 2011/146942 A1 | 11/2011 |

OTHER PUBLICATIONS

Yuan et al. Journal of Biological Chemistry 284 (46) : 31672 (2009).*
Fire et al., Rolling Replication of Short DNA Circles. PNAS 92 : 4641 (1995).*
Hatch et al., Rolling circle amplification of DNA immobilized on solid surfaces and its application to multiplex mutation detection. Genetic Analysis: Biomolecular Engineering 15 : 35 (1999).*
Mullis et al., Specific Enzymatic Amplification of DNA In Vitro: The Polymerase Chain Reaction. Cold Spring Harbor Symposia on Quantitative Biology, vol. LI : 263 (1986).*
Jonstrup et al., A microRNA detection system based on padlock probes and rolling circle amplification. RNA 12 : 1747 (2006).*
Noir et al., Oligonucleotide-Oligospermine Conjugates (Zip Nucleic Acids): A Convenient Means of Finely Tuning Hybridization Temperatures. JACS 130 :13500 (2008).*
Dahl et al., "Circle-to-circle amplification for precise and sensitive DNA analysis," Proc. of the Nat'l Acad. of Sciences, Mar. 30, 2004, 101(13), pp. 4548-4553.
European Patent Office, Extended European Search Report in European Patent Application No. 13171353.9, Jul. 31, 2013, 7 pp.
Linsen et al., "Limitations and possibilities of small RNA digital gene expression profiling", Nature Methods, 6(7): 474-476 (2009).
Kumar et al., "miR-ID: A novel, circularization-based platform for detection of microRNAs," RNA, 17(2), 366-380 (2010).
Primer3 Input, downloaded from <<http://bioinfo.ut.ee/primer3-0.4.0/primer3/>> on Dec. 19, 2014.
Reichenstein et al. "A novel qPCR assay for viral encoded microRNAs", Journal of Virological Methods, 163, 323-328 (2010).

* cited by examiner

Primary Examiner — Ethan C Whisenant
(74) Attorney, Agent, or Firm — Leydig, Voit & Mayer, Ltd.

(57) ABSTRACT

Provided is a dual-hybridization polynucleotide including a first complementary region that is complementary to the 3'-terminus of a target nucleic and a second complementary region that is complementary to the 5'-terminus of the target nucleic acid, a composition and kit including the polynucleotide, and a method of producing a nucleotide sequence complementary to the target nucleic acid. The first complementary region to be bound at the 3'-terminus of the target nucleic acid can be shortened and the target nucleic acid may be amplified with excellent specificity and/or sensitivity.

11 Claims, 5 Drawing Sheets

POLYNUCLEOTIDE AND USE THEREOF

CROSS-REFERENCE TO RELATED APPLICATION

This application claims the benefit of Korean Patent Application No. 10-2012-0131026, filed on Nov. 19, 2012 in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide sequence listing submitted concurrently herewith and identified as follows: One 33,313 Byte ASCII (Text) file named "712236_ST25.txt," created on May 21, 2013.

BACKGROUND

1. Field

The present disclosure relates to polynucleotides including complementary regions that are complementary to the 3'-terminal and the 5'-terminal of a target nucleic acid and uses thereof.

2. Description of the Related Art

Methods of amplifying nucleic acids include extending a nucleotide sequence from the 3'-terminus of a primer in the presence of a nucleic acid polymerase. The primer includes a sequence complementary to that of a target nucleic acid. To extend the nucleotide sequence, the primer and the target nucleic acid need to specifically and stably hybridize with each other. The design of a primer for a short nucleic acid presents difficulties. The stability of the hybridized product of nucleic acids is known to be proportionate to the length of a complementary sequence. In addition, if the length of a primer increases, the length of a target nucleic acid to be amplified shortens. Therefore, there is still a need to develop a polynucleotide primer that specifically and stably binds to a short target nucleic acid. There is also a need to develop a polynucleotide that provides increased specificity for the amplified target nucleic acid as well.

SUMMARY

The disclosure provides a dual-hybridization polynucleotide including regions that are complementary to the 3'-terminus and the 5'-terminus of a target nucleic acid. Also, provided are compositions and kits for amplifying a target nucleic acid that include one or more dual-hybridization polynucleotides having regions that are complementary to the 3'-terminus and the 5'-terminus of a target nucleic acid.

The disclosure also provides methods of producing a dual-hybridization polynucleotide including a nucleotide sequence that is complementary to a target nucleic acid using a polynucleotide including complementary regions that are complementary to the 3'-terminus and the 5'-terminus of a target nucleic acid.

Additionally the disclosure provides a method for amplifying a target nucleic acid that includes hybridizing the target nucleic acid to a dual-hybridization polynucleotide including complementary regions that are complementary to the 3'-terminus and the 5'-terminus of a target nucleic acid. The amplification method can be reverse transcription (RT), polymerase chain reaction (PCR), quantitative PCR (qPCR), RT-PCR, and RT-qPCR.

BRIEF DESCRIPTION OF THE DRAWINGS

These and/or other aspects will become apparent and more readily appreciated from the following description of the embodiments, taken in conjunction with the accompanying drawings in which:

FIG. 1A is a schematic view illustrating a dual-hybridization polynucleotide "2" according to an embodiment of the present invention and a method of using the dual-hybridization polynucleotide to produce an amplified polynucleotide "3" comprising nucleotide sequence complementary to a target nucleic acid "1", according to an embodiment of the present invention. FIG. 1B is a schematic view illustrating a dual-hybridization polynucleotide according to an embodiment of the present invention that includes a 5' overhang region "2c" that is not complementary to the target sequence "1". FIG. 1C is a schematic view illustrating an amplified polynucleotide "3" comprising a region that is complementary to target nucleic acid "1" in FIG. 1B and region "2c" that is not complementary to the target sequence "1" in FIG. 1B.

DETAILED DESCRIPTION

Figure 1:
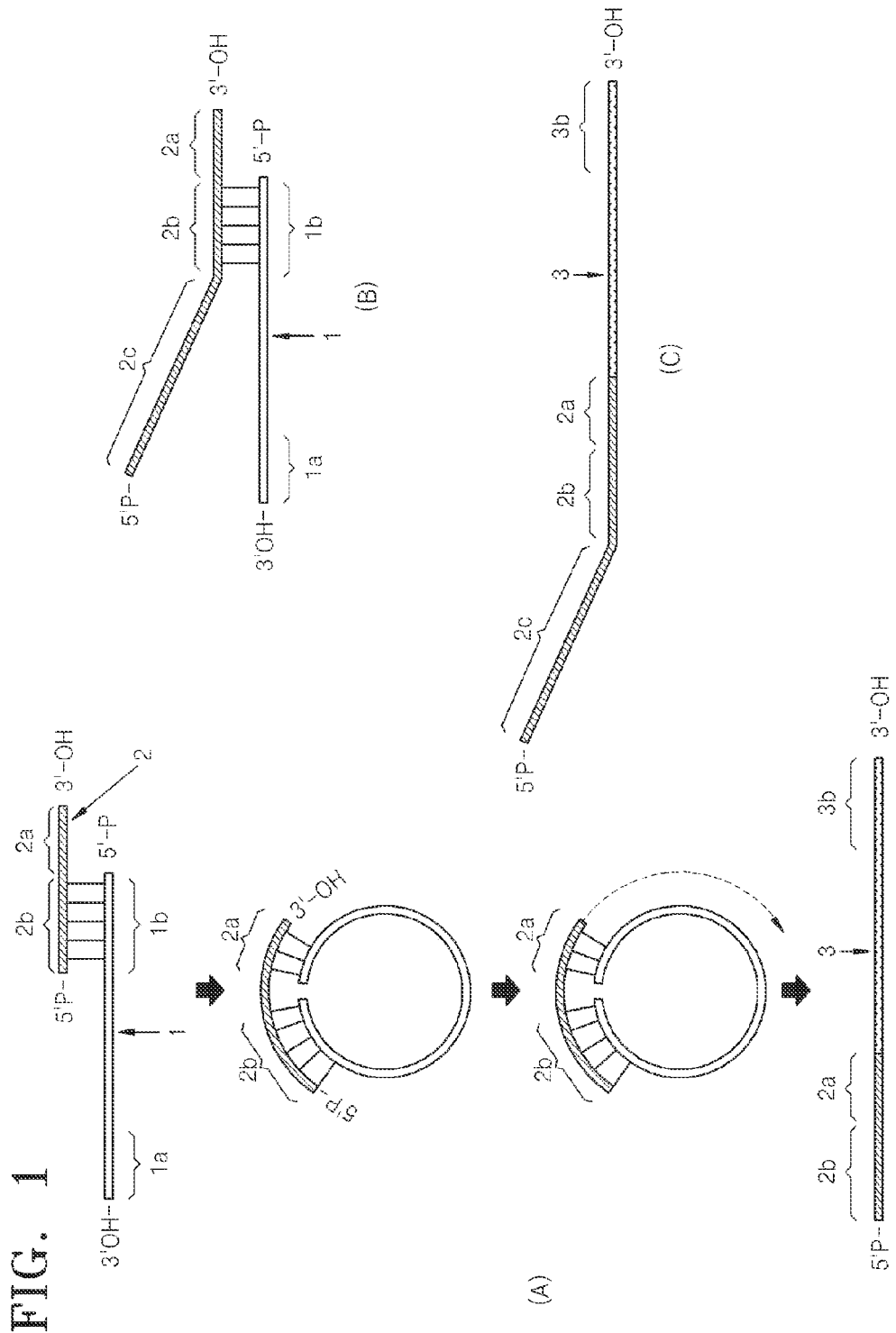
FIG. 1 includes three panels (FIGS. 1A, 1B, and 1C).

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list. As used herein, the term "dual-hybridization polynucleotide" refers to a polynucleotide that includes a first region that is complementary to the 3'-terminal region of a target sequence and a second region that is complementary to the 5'-terminal region of the target sequence.

According to an embodiment of the present invention, a dual-hybridization polynucleotide includes a first complementary region that is complementary to at least two consecutive nucleotides on the 3'-terminus of a target nucleic acid and a second complementary region that is complementary to at least two consecutive nucleotides on the 5'-terminus of a target nucleic acid. The first complementary region is located at the 3'-terminal side of the second complementary region in the dual-hybridization polynucleotide. In other words, the dual-hybridization polynucleotide may have the configuration 5'-(second complementary region)-(first complimentary region)-3'. Thus, the dual-hybridization polynucleotide can hybridize to the 5'-terminus and the 3'-terminus of the target nucleic acid to create a circularized construct as depicted in FIG. 1.

The first complementary region of the polynucleotide may be complementary to at least two consecutive nucleotides from the 3'-terminal of the target nucleic acid. For example, the first complementary region of the polynucleotide may be complementary to 2 nucleotides (nt), 3 nt, 4 nt, 5 nt, 6 nt, or 7 nt from the 3'-terminal of the target nucleic acid. For example, the length of the first complementary region may be 2 nt to 7 nt. The first complementary region may include a DNA, RNA, peptide nucleic acid (PNA), locked nucleic acid (LNA), ZIP nucleic acid (ZNA) or nucleotide analogue.

The second complementary region of the dual-hybridization polynucleotide may be complementary to at least two consecutive nucleotides from the 5'-terminus of the target nucleic acid. For example, the second complementary region of the polynucleotide may be complementary to 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, or 20 nt from 5'-terminus of the target nucleic acid. For example, the length of the second complementary region may be 3 nt to 20 nt. The second complementary region may include DNA, RNA, peptide nucleic acid (PNA), locked nucleic acid (LNA), ZIP nucleic acid (ZNA) or nucleotide analogue.

The first complementary region of the polynucleotide may be located at the 3'-terminal side of the second complementary region. The first complementary region and the second complementary region may be contiguous to each other (directly adjacent without separation), or the first and second complementary regions may be separated from each other by an intervening linker or spacer of at least one nucleotide in length.

One of the first or second complimentary regions of the dual hybridization probe may contain a sequence complimentary to the inverse sequence of the target nucleic acid, such that the probe bound to the target forms a circularized construct. Thus, for instance, if the first complimentary region comprises a sequence complimentary to the sequence of the 3' terminus of the target nucleic acid as read in the 5'-3' direction, the second complimentary region may comprise a sequence complimentary to the inverse sequence of the 5' terminus of the target nucleic acid.

The dual-hybridization polynucleotide may be DNA or RNA. Additionally, the dual-hybridization polynucleotide can include nucleotide analogues, for example PNA and LNA. For example, the second complementary region of the polynucleotide may include a nucleotide analogue, for example, PNA and LNA. The nucleotide analogue, for example, PNA and LNA, may also be included not only in the second complementary region but also in the first complementary region. The polynucleotide may be single-stranded. The length of the polynucleotide can be 7 nt to 200 nt, 7 nt to 180 nt, 7 nt to 150 nt, 7 nt to 130 nt, 7 nt to 100 nt, 7 nt to 80 nt, 7 nt to 50 nt, 7 nt to 30 nt, 7 nt to 20 nt, 7 nt to 15 nt, or 10 nt to 40 nt.

The target nucleic acid may be DNA, RNA, or a chimera of DNA and RNA. The target nucleic acid may be single-stranded or double-stranded. The length of the target nucleic acid may be 10 nt to 500 nt, 15 nt to 200 nt, 15 nt to 180 nt, 15 nt to 150 nt, 15 nt to 130 nt, 15 nt to 100 nt, 15 nt to 80 nt, 15 nt to 50 nt, 15 nt to 40 nt, or 15 nt to 30 nt. The target nucleic acid may be small RNA. For example, the small RNA may be non-coding RNA, micro RNA (miRNA), small interfering RNA (siRNA), tRNA, or decapping mRNA. Natural mRNA of eukaryotic cells has a 5'-cap. However, mRNA may be degraded during storage or processing of a biological sample and/or during isolation of mRNA from a biological sample. In this case, the isolated target nucleic acid may not have the 5'-cap of the natural mRNA. The 5'-cap is a structure in which a 7-methylguanylate is connected to 5'-OH of ribose sugar of the 5'-end of an mRNA via a triphosphate linkage or a structure of which a guanylate, as a decomposition product of the linkage, is connected to 5'-OH of ribose sugar of the 5'-end of an mRNA. In addition, the target nucleic acid, which can be RNA having at least 200 nucleotides, may be RNA having a region where a sequence of 30 consecutive nucleotides has GC contents of less than 30% or of at least 80%. The target nucleic acid can be RNA including at least 5 consecutive nucleotides having complementary sequences in molecules so as to form an intramolecular secondary structure, RNA including at least 5 consecutive nucleotides that are complementary to each other. The target nucleic acid can include any combination of the foregoing properties.

In some embodiments, the dual-hybridization polynucleotide of the invention, may further include a third region that is not complementary to the target nucleic acid present. For example, the third region may be located at the 5'-terminal side of the second complementary region. Thus, for example, the polynucleotide may include the following structure, starting at the 5'-terminus: the third region is linked to the second complementary region, which is linked to the first complementary region located at the 3' terminus of the dual-hybridization polynucleotide. The length of the third region of the polypeptide may be from 3 nt to 200 nt. Examples of the third region may include 3 nt to 200 nt, 3 nt to 180 nt, 3 nt to 150 nt, 3 nt to 130 nt, 3 nt to 100 nt, 3 nt to 80 nt, 3 nt to 50 nt, 3 nt to 40 nt, or 3 nt to 30 nt. The third region may include a primer sequence, a restriction enzyme recognition site, or a probe-binding site. The third region may include DNA, RNA, peptide nucleic acid (PNA), locked nucleic acid (LNA), ZIP nucleic acid (ZNA), or nucleotide analogue. The third region and the second complementary region may be contiguous to each other or they may be separated from each other by a linker of at least 1 nt in length. For example, the linker may include a primer-binding site, a restriction enzyme recognition site, or a probe-binding site.

The dual-hybridization polynucleotide may act as a primer in template-dependent nucleic acid synthesis, wherein the template is the target sequence. Thus, the polynucleotide may be used as a primer. The dual-hybridization polynucleotide may also be used as a probe for confirming the presence of the target nucleic acid in a sample. The dual-hybridization polynucleotide can include a probe binding site that is, for example, 5 nt to 195 nt in length. The probe-binding site is not homologous or complementary to the target sequence. The dual-hybridization polynucleotide can be used to introduce the probe binding site into amplified target sequence, which facilitates detection or purification of the amplified target sequence. Alternatively, the probe binding site can be used to detect the presence of a target sequence that is bound to the dual-hybridization polynucleotide without amplification.

The dual-hybridization polynucleotide may have the second complementary region positioned between the first complementary region and the third region so as to shorten the length of the first complementary region and to increase the length of DNA generated by reverse transcription. As the length of reverse transcribed DNA is increased, so does the ability to design a good PCR primer that is specific to the reverse transcribed DNA and thereby facilitate specific detection of target sequence RNA. Moreover, the presence of the second complementary region can improve sensitivity and specificity for the detection of the target nucleic acid, as demonstrated in the Examples provided herein.

According to another embodiment, the present invention provides a composition that includes the dual-hybridization polynucleotide described herein. In some embodiments, the composition can further include the target nucleic acid described herein. For example, the composition can include the dual-hybridization polynucleotide hybridized to the target nucleic acid.

The composition can be isolated or purified. As used herein, "isolated" can refer to a biologically or chemically synthesized dual-hybridization polynucleotide which is considerably free of contaminants or materials (e.g., cell components or synthetic reagents) that would interfere with their use in the methods of the invention. "Isolated" can also refer to a target sequence nucleic acid that is considerably free from components which normally accompany or interact with the nucleic acid in its naturally occurring environment (e.g., in a biological sample containing the nucleic acid). An isolated dual-hybridization polynucleotide or an isolated target sequence nucleic acid can be considerably (e.g., at least about 60%, at least about 65%, at least about 70%, at least about 75%, at least about 80%, at least about 85%, at least about 90%, at least about 95%, at least about 96%, at least about 97%, at least about 98%, or at least about 99%) free from such contaminants, materials, or components.

The composition can be a composition for amplifying the target nucleic acid. The amplification reaction can be a method of amplifying nucleic acids, such as by DNA amplification or RNA amplification. The amplification reaction may be performed under thermal cycling or isothermal conditions. Examples of the amplification reaction include a polymerase chain reaction (PCR), nucleic acid sequence-based amplification (NASBA), ligase chain reaction (LCR), strand displacement amplification (SDA), rolling circle amplification (RCA), and the like. Also, the amplification reaction can be a method of amplifying RNA, for example, the amplification reaction can include reverse transcription (RT), RT-PCR or RT-qPCR. The amplification reaction includes increasing the initial copy number of target nucleic acid sequences or sequences complementary thereto. The term "PCR" used herein refers to a method of amplifying a target nucleic acid using a polymerase to extend primer pairs that specifically bind to the target nucleic acid.

Thus, the invention provides a composition that includes the dual-hybridization polynucleotide described herein and further includes a material or reagent for the amplification of the target nucleic acid. For example, the composition may further include one or more of the following materials or reagents for the amplification of a target nucleic acid: a nucleic acid polymerase, a buffer for the activity of the nucleic acid polymerase, a cofactor (e.g. magnesium), a substrate and/or a target sequence described herein. The nucleic acid polymerase may be one selected from a DNA polymerase, an RNA polymerase, a reverse transcriptase, and a combination thereof. The term "reverse transcription" may refer to the synthesis of DNA strands that are complementary to RNA sequences by using RNA as a template. The nucleic acid polymerase may have strand displacement activity. For example, the nucleic acid polymerase may be at least one reverse transcriptase derived from retrovirus, for example, HIV, MMLV, or AMV. The nucleic acid polymerase may 3'→5' exonuclease activity-free. The composition may include a material for reverse transcription or PCR amplification.

According to another embodiment of the present invention, there is provided a kit for amplifying a target nucleic acid, the kit including a dual-hybridization polynucleotide described herein and one or more materials or reagents for the amplification and/or detection of the target nucleic acid described herein. The kit can include the dual-hybridization polynucleotide and can further include one or more materials or reagents for the amplification of the target nucleic acid that are suitably packaged, for example, in vials. The kit can include the dual-hybridization polynucleotide and materials or reagents for PCR, NASBA, an LCR, SDA, RCA, and the like. Also, in some embodiments of the invention, the kit can include the dual-hybridization polynucleotide and materials or reagents for amplifying RNAs such as, for example, by RT, RT-PCR, or RT-qPCR.

Materials or reagents for the amplification of the target nucleic acid can include, for example, a nucleic acid polymerase, a suitable buffer for the activity of the nucleic acid polymerase, a cofactor, and/or a substrate. The kit may include one or more target nucleic acids, which can be used, for example, as controls. The target nucleic acid is packaged separately from the dual-hybridization polynucleotide in the kit. The nucleic acid polymerase included in the kit can be a DNA polymerase, an RNA polymerase, a reverse transcriptase, or a combination thereof. The nucleic acid polymerase may have strand displacement activity. The nucleic acid polymerase may be at least one reverse transcriptase derived from retrovirus, for example, HIV, MMLV, or AMV. The nucleic acid polymerase may be deficient of 3'→5' exonuclease activity. The kit may further include instructions for amplifying the target nucleic acid using a dual-hybridization polynucleotide described herein.

The invention provides a method of designing and producing a dual-hybridization polynucleotide. The method includes providing the sequence of a target nucleic acid, as described herein, and determining the sequence of a first complementary region that is complementary to at least two consecutive nucleotides from the 3'-terminus of a target nucleic acid. The method also includes determining the sequence of a second complementary region that is complementary to at least two consecutive nucleotides from the 5'-terminus of the target nucleic acid. The method further includes designing and producing any of the dual-hybridization polynucleotides described herein, which have the first complementary region located at the 3'-terminal side of the second complementary region. The method can further include designing and producing the dual-hybridization polynucleotide to include a third region (e.g., a primer sequence, a restriction enzyme recognition site, or a probe-binding site) that is not complementary to the target nucleic acid and which is present at the 5'-terminal side of the second complementary region.

According to another embodiment of the present invention, there is provided a method of producing a nucleotide sequence complementary to a target nucleic acid. The method includes hybridizing a target nucleic acid described herein to a dual-hybridization polynucleotide described herein that includes a first complementary region that is complementary to at least two consecutive nucleotides of the 3'-terminus of a target nucleic acid and a second complementary region that is complementary to at least two consecutive nucleotide from the 5'-terminus of a target nucleic acid, wherein the first complementary region is present at the 3'-terminal side of the second complementary region. The method further includes incubating the hybridized sample in the presence of a nucleic acid polymerase under conditions suitable to produce a nucleotide sequence complementary to the target nucleic acid. Typically, the nucleic acid polymerase initiates the synthesis of the complementary sequence starting from the 3'-terminus of the dual-hybridization polynucleotide.

The method can include hybridizing the target nucleic acid to a dual-hybridization polynucleotide described herein including a first complementary region that is complementary to at least 2, 3, 4, 5, 6, or 7 consecutive nucleotides of the 3'-terminus of a target nucleic acid and a second complementary region that is complementary to at least 2, 3, 4, 5, 6, 7, 8, 9, 10, 11, 12, 13, 14, 15, 16, 17, 18, 19, or 20 consecutive nucleotides from the 5'-terminus of a target nucleic acid, wherein the first complementary region is linked to the 3'-terminal side of the second complementary region.

The hybridizing process may be performed by a suitable method. For example, the hybridizing process may be performed by incubating the dual-hybridization polynucleotide and the target nucleic acid in a known buffer appropriate for the hybridization of nucleic acids. The hybridizing process may be performed at an appropriate temperature ranging from about 0° C. to about 25° C., for example, about 4° C. The hybridizing temperature may be appropriately adjusted according to the sequences and lengths of selected polynucleotide and target nucleic acid. The hybridizing process may be performed for an appropriate time period, for example, about 1 to about 12 hours (overnight).

The method includes incubating the hybridized sample in the presence of a nucleic acid polymerase to produce a nucleic sequence complementary to the target nucleic acid by initiating synthesis of the complementary strand from the 3'-terminal of the dual-hybridization polynucleotide.

The nucleic acid polymerase may be one selected from a DNA polymerase, an RNA polymerase, a reverse transcriptase, and a combination thereof. The term "reverse transcription" may refer to the synthesis of DNA strands that are complementary to RNA sequences by using RNA as a template. The nucleic acid polymerase may have strand displacement activity. For example, the nucleic acid polymerase may be a reverse transcriptase derived from retrovirus, for example, HIV, MMLV, or AMV. The nucleic acid polymerase may be deficient in 3'→5' exonuclease activity.

The incubating process may be performed under conditions appropriate for the activity of the nucleic acid polymerase. The incubating process may be performed in the presence of the nucleic acid polymerase, a buffer for the activity of the nucleic acid polymerase, a cofactor, and a substrate for the enzymes. For example, the incubating process may be performed in the presence of material for RT or PCR amplification.

During the incubating process, the nucleotide sequence complementary to the target nucleic acid may be produced by the nucleic acid polymerase extending the 3'-terminus of the dual-hybridization polynucleotide. The nucleic acid polymerase can also displace the 5'-terminus of the polynucleotide hybridized with the target nucleic acid and produce a sequence that is complementary to the entire target nucleic acid.

The invention also provides a method of determining whether the target sequence is present in a sample. The method includes performing the method of producing a nucleotide sequence complementary to a target nucleic acid described herein and further includes determining whether or not the produced product, i.e., the nucleotide sequence complementary to the target nucleic acid, is present. A determination that the product (nucleotide sequence complementary to the target nucleic acid) is present indicates that the target nucleic acid exists in a sample. Otherwise, if the produced product is not found to be present, the method indicates that the target nucleic acid does not exist in the sample.

In addition, the method may further include amplifying a nucleic acid by using the produced product, i.e., the nucleotide sequence complementary to the target nucleic acid as a template. The amplifying process may be performed by a known method. Exemplary amplifying reactions are described above and in the following examples.

The method described herein involves the formation of a circularized hybridization complex comprising the dual hybridization probe comprising a first complementary region and a second complementary region located 3' of the second complementary region, and the polynucleotide target, wherein the first complimentary region of the probe is hybridized to the to the 3' terminus of the target, and the second complimentary region of the probe is hybridized to the 5' terminus of the target. The hybridization complex is, thus, considered an additional aspect of the invention. All other aspects of the dual hybridization probe and target nucleic acid are as described herein with respect to the other aspects of the invention.

One or more embodiments of the present invention will now be described more fully with reference to the following examples. However, these examples are provided only for illustrative purposes and are not intended to limit the scope of the invention.

Example 1

Preparation of Dual-Hybridization Reverse Transcription Primers

A nucleic acid sequence complementary to a target nucleic acid was produced from the 3'-terminus of a dual-hybridization polynucleotide (hereinafter, referred to as "dual-hybridization primer" or "dual-hybridization reverse transcription (RT) primer") including a first complementary region that is complementary to at least two consecutive nucleotides from the 3'-terminus of a target nucleic acid; and a second complementary region that is complementary to at least two consecutive nucleotides from the 5'-terminus of a target nucleic acid, wherein the first complementary region is present at the 3'-terminal side of the second complementary region. As a control, a general primer having no second complementary region (hereinafter, referred to as "linear primer" or "3' priming RT primer") was used. The dual-hybridization RT primer includes a third region that is not complementary to the target nucleic acid. The third region is present in the 5'-terminal side of the second complementary region. The third region that is not complementary to the target nucleic acid includes a universal PCR primer sequence.

In FIG. 1, the "1" indicates the target nucleic acid. The "1a" represents the 3'-terminal sequence of the target nucleic acid having a nucleic acid sequence complementary to the "2a" sequence discussed below. The "1b" represents the 5'-terminus of the target nucleic acid having a nucleic acid sequence complementary to the "2b" sequence discussed below. In FIG. 1, the "2" indicates the dual-hybridization RT primer. The "2a" represents the 3'-terminal sequence of the dual-hybridization RT primer (the first complementary region) having a nucleic acid sequence complementary to 1a. The "2b" represents the 5'-terminus of the dual-hybridization RT primer (the second complementary region) having a nucleic acid sequence complementary to 1b. In FIG. 1B, "2c" represents a third region of a dual-hybridization RT primer that includes a PCR primer sequence that is not complementary to the target nucleic acid. In FIG. 1C, the "3" represents DNA synthesized by an RT enzyme using the dual-hybridization RT primer shown in FIG. 1(B). The "3b" represents a nucleic acid sequence complementary to the 1b sequence. "3b" is generated when the RT enzyme displaces the hybridized primer sequence 2b to produce new sequence that is complementary to 1b.

Example 2

Effect of Detection of Target Nucleic Acids by Dual-Hybridization RT Primers

Methods of detecting target nucleic acids using a dual-hybridization RT primer and a control 3' priming RT primer, respectively, were compared.

Sequences of the target nucleic acid miRNAs, control 3' priming RT primers, dual-hybridization RT primers, and miRNA-specific PCR primers are shown in Table 1.

TABLE 1

| microRNA ID | RNA | 3' priming RT primer | Dual-hybridization RT primer | miRNA-specific PCR primer |
|---|---|---|---|---|
| let-7b-5p | 5'-UGAGGUAGUAGGUUGUGUGGUU-3' (SEQ ID. NO: 1) | 5'-CGGTGAGGTCTTTGGTTCATAACCAC-3' (SEQ ID. NO: 2) | 5'-CGGTGAGGTCTTTGGTTCATCTACCTCAAACC-3' (SEQ ID. NO: 3) | 5'-CGCTGAGGTAGTAGGTTGTG-3' (SEQ ID. NO: 4) |
| let-7d-5p | 5'-AGAGGUAGUAGGUUGCAUAGUU-3' (SEQ ID. NO: 5) | 5'-CGGTGAGGTCTTTGGTTCATAACTAT-3' (SEQ ID. NO: 6) | 5'-CGGTGAGGTCTTTGGTTCATCTACCTCTAACT-3' (SEQ ID. NO: 7) | 5'-CGCAGAGGTAGTAGGTTGC-3' (SEQ ID. NO: 8) |
| miR-100-5p | 5'-AACCCGUAGAUCCGAACUUGUG-3' (SEQ ID. NO: 9) | 5'-CGGTGAGGTCTTTGGTTCATCACAAG-3' (SEQ ID. NO: 10) | 5'-CGGTGAGGTCTTTGGTTCATCGGGTTCACA-3' (SEQ ID. NO: 11) | 5'-CAACCCGTAGATCCGAA-3' (SEQ ID. NO: 12) |
| miR-10a-5p | 5'-UACCCUGUAGAUCCGAAUUUGUG-3' (SEQ ID. NO: 13) | 5'-CGGTGAGGTCTTTGGTTCATCACAAA-3' (SEQ ID. NO: 14) | 5'-CGGTGAGGTCTTTGGTTCATAGGGTACACA-3' (SEQ ID. NO: 15) | 5'-CGTACCCTGTAGATCCGAA-3' (SEQ ID. NO: 16) |
| miR-122-5p | 5'-UGGAGUGUGACAAUGGUGUUUG-3' (SEQ ID. NO: 17) | 5'-CGGTGAGGTCTTTGGTTCATCAAACA-3' (SEQ ID. NO: 18) | 5'-CGGTGAGGTCTTTGGTTCATACACTCCACAAA-3' (SEQ ID. NO: 19) | 5'-CGTGGAGTGTGACAATGG-3' (SEQ ID. NO: 20) |
| miR-125b-5p | 5'-UCCCUGAGACCCUAACUUGUGA-3' (SEQ ID. NO: 21) | 5'-CGGTGAGGTCTTTGGTTCATTCACAA-3' (SEQ ID. NO: 22) | 5'-CGGTGAGGTCTTTGGTTCATCTCAGGGATCAC-3' (SEQ ID. NO: 23) | 5'-CGTCCCTGAGACCCTAAC-3' (SEQ ID. NO: 24) |
| miR-130a-3p | 5'-CAGUGCAAUGUUAAAAGGGCAU-3' (SEQ ID. NO: 25) | 5'-CGGTGAGGTCTTTGGTTCATATGCCC-3' (SEQ ID. NO: 26) | 5'-CGGTGAGGTCTTTGGTTCATGCACTGATGC-3' (SEQ ID. NO: 27) | 5'-GCGCAGTGCAATGTTAAA-3' (SEQ ID. NO: 28) |

TABLE 1 -continued

| microRNA ID | RNA | 3' priming RT primer | Dual-hybridization RT primer | miRNA-specific PCR primer |
|---|---|---|---|---|
| miR-135a-5p | 5'-UAUGGCUUUUU AUUCCUAUGUGA-3' (SEQ ID. NO: 29) | 5'-CGGTGAGGTCT TTGGTTCATTCA CAT-3' (SEQ ID. NO: 30) | 5'-CGGTGAGGTCT TTGGTTCATAAG CCATATCAC-3' (SEQ ID. NO: 31) | 5'-CGCTATGGCTTT TTATTCCT-3' (SEQ ID. NO: 32) |
| miR-135b-5p | 5'-UAUGGCUUUUC AUUCCUAUGUGA-3' (SEQ ID. NO: 33) | 5'-CGGTGAGGTCT TTGGTTCATTCA CAT-3' (SEQ ID. NO: 34) | 5'-CGGTGAGGTCT TTGGTTCATGCC ATATCAC-3' (SEQ ID. NO: 35) | 5'-CGTATGGCTTTT CATTCCT-3' (SEQ ID. NO: 36) |
| miR-15b-5p | 5'-UAGCAGCACAU CAUGGUUUACA-3' (SEQ ID. NO: 37) | 5'-CGGTGAGGTCT TTGGTTCATTGT AAA-3' (SEQ ID. NO: 38) | 5'-CGGTGAGGTCT TTGGTTCATCTG CTATGTA-3' (SEQ ID. NO: 39) | 5'-CGTAGCAGCACA TCATGG-3' (SEQ ID. NO: 40) |
| miR-20a-5p | 5'-UAAAGUGCUUA UAGUGCAGGUAG-3' (SEQ ID. NO: 41) | 5'-CGGTGAGGTCT TTGGTTCATCTA CCT-3' (SEQ ID. NO: 42) | 5'-CGGTGAGGTCT TTGGTTCATGCA CTTTACTAC-3' (SEQ ID. NO: 43) | 5'-CCGCTAAAGTGC TTATAGTGC-3' (SEQ ID. NO: 44) |
| miR-214-3p | 5'-ACAGCAGGCAC AGACAGGCAGU-3' (SEQ ID. NO: 45) | 5'-CGGTGAGGTCT TTGGTTCATACT GCC-3' (SEQ ID. NO: 46) | 5'-CGGTGAGGTCT TTGGTTCATCCT GCTGTACTG-3' (SEQ ID. NO: 47) | 5'-CACAGCAGGCA CAGACA-3' (SEQ ID. NO: 48) |
| miR-29a-3p | 5'-UAGCACCAUCU GAAAUCGGUUA-3' (SEQ ID. NO: 49) | 5'-CGGTGAGGTCT TTGGTTCATTAA CCG-3' (SEQ ID. NO: 50) | 5'-CGGTGAGGTCT TTGGTTCATTGG TGCTATAAC-3' (SEQ ID. NO: 51) | 5'-CGCTAGCACCAT CTGAAAT-3' (SEQ ID. NO: 52) |
| miR-34a-5p | 5'-UGGCAGUGCU UAGCUGGUUGU-3' (SEQ ID. NO: 53) | 5'-CGGTGAGGTCT TTGGTTCATACA ACC-3' (SEQ ID. NO: 54) | 5'-CGGTGAGGTCT TTGGTTCATCAC TGCCAACAA-3' (SEQ ID. NO: 55) | 5'-GCCTGGCAGTG TCTTAGC-3' (SEQ ID. NO: 56) |
| miR-517c-3p | 5'-AUCGUGCAUCC UUUUAGAGUGU-3' (SEQ ID. NO: 57) | 5'-CGGTGAGGTCT TTGGTTCATACA CTC-3' (SEQ ID. NO: 58) | 5'-CGGTGAGGTCT TTGGTTCATTGC ACGATACAC-3' (SEQ ID. NO: 59) | 5'-CGATCGTGCATC CTTTTA-3' (SEQ ID. NO: 60) |

In addition, the sequence of the universal PCR primer used was 5'-CGGTGAGGTCTTTGGTTCAT-3' (SEQ ID. NO: 61).

The length of the first complementary region of the dual-hybridization RT primer is 4 nt and that of the second complementary region is 4 nt to 8 nt.

The detection of each target nucleic acid by dual-hybridization RT primer was done by RT-PCR. SuperScript III reverse transcriptase (Invitrogen) was used to convert miRNA to cDNA. For the RT reaction, 12 μl of an RT master mixture (5 μl of water, 2 μl of a 5× buffer solution (Invitrogen), 2 μl of 15 mM MgCl2, 1 μl of 0.1 M dithiothreitol (DTT), 1 μl of 10 mM dNTPs, 1 μl of RNAseOUT (Invitrogen), and 1 μl of SuperScript III enzyme was mixed in a 96-well plate with 2 μl of 10 uM dual-hybridization RT primer and 5 μl of miRNA template. The RT reaction was incubated at 16° C. for 30 minutes, 42° C. for 1 hour, and 70° C. for 15 minutes following a 5-fold dilution with 80 μl of TE (10 mM Tris at a pH of 7.6, 0.1 mM EDTA). After the RT reaction, 5 μl of each RT reaction product containing cDNA was analyzed (and repeated 3 times) by quantitative PCR (qPCR) in a 96-well optical PRC plate using Light Cycler® 480 (LC 480) PCR device (Hoffmann La-Roche Ltd., Indianapolis, Ind.). The qPCR reaction mixture included 10 μl of a 2×SYBR green PCR master mixture (Exiqon), 0.1 μl of 10 μM universal primer, 0.1 μl of 10 μM miRNA-specific primer, 4.8 μl of water and 5 μl of RT reaction product sample to make a total qPCR volume of 20 μl. The qPCR was performed using the conditions suggested by a manufacturer, and then dissociation melting curves were analyzed to confirm the amplicon types generated by qPCR reaction. Crossing point (Cp) values were determined using the manufacturer's software provided with LC 480 device.

Figure 2:
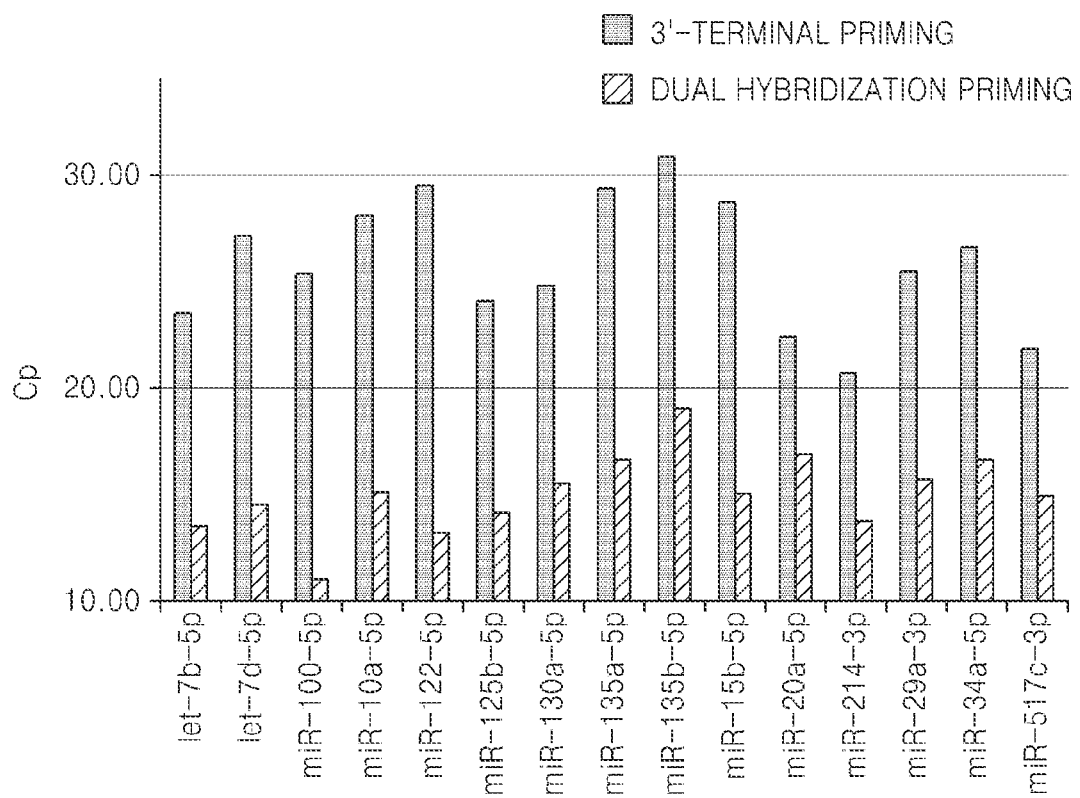
FIG. 2 is a bar graph illustrating the priming effect of dual-hybridization polynucleotides according to the present invention relative to the priming effect of control 3'-terminal primers. The microRNA (miRNA) target sequences indicated on the x-axis were analyzed by reverse transcription and quantitative polymerase chain reaction (RT-qPCR). Crossing point (Cp) value for each qPCR product is shown on the y-axis.

FIG. 2 depicts the priming effect of the dual-hybridization RT primers in Table 1 (hatched bars) and their ability to amplify the miRNA templates indicated on the x-axis of the graph in FIG. 2. FIG. 2 also illustrates the priming effect of control 3' priming RT primers (shaded bars) and their ability to amplify the miRNA templates indicated on the x-axis. Cp values on the Y-axis represent the crossing point (PCR cycle number) when RT-PCR product signal was detected. As shown in FIG. 2, when the dual-hybridization RT primer was used, Cp values were significantly decreased as compared to the 3' priming RT primer. The decreased Cp values demonstrate the improved detection of target nucleic acids, including miRNAs, that can be achieved using the dual-hybridization polynucleotides and methods disclosed by the invention.

Example 3

Detection of Target Nucleic Acids Using Different Lengths of the First Complementary Region and Different Lengths of the Second Complementary Region in a Dual-Hybridization Polynucleotide Detection of a target nucleic acid was evaluated using dual-hybridization polynucleotides having different lengths (nt number) of the first complementary region and/or different lengths of the second complementary region.

The target nucleic acid (miRNA) had the sequence: 5'-CGGUGAGGUCUUUGGUUCAUUAGCAG-CACGUAAAUAUUGGCG-3'(SEQ ID. NO: 62), miRNA-specific PCR primer had the sequence: 5'-CGCGCTAGCA-GCACGTAAAT-3' (SEQ ID. NO: 63), and the universal PCR primer had the sequence: 5'-GTGCAGGGTC-CGAGGT-3' (SEQ ID. NO: 64).

Sequences of 3' priming RT primers, and dual-hybridization RT primers are shown in Table 2. The single underlined part of the nucleic acid sequences indicates the first complementary region complementary to the 3'-terminus of the target nucleic acid. The double underlined part of the nucleic acid sequences indicates the second complementary region complementary to the 5'-terminus of the target nucleic acid Detection results of the target nucleic acids according to the lengths of the first complementary region and the second complementary region were confirmed according to the qPCR method of Example 2.

Figure 3:
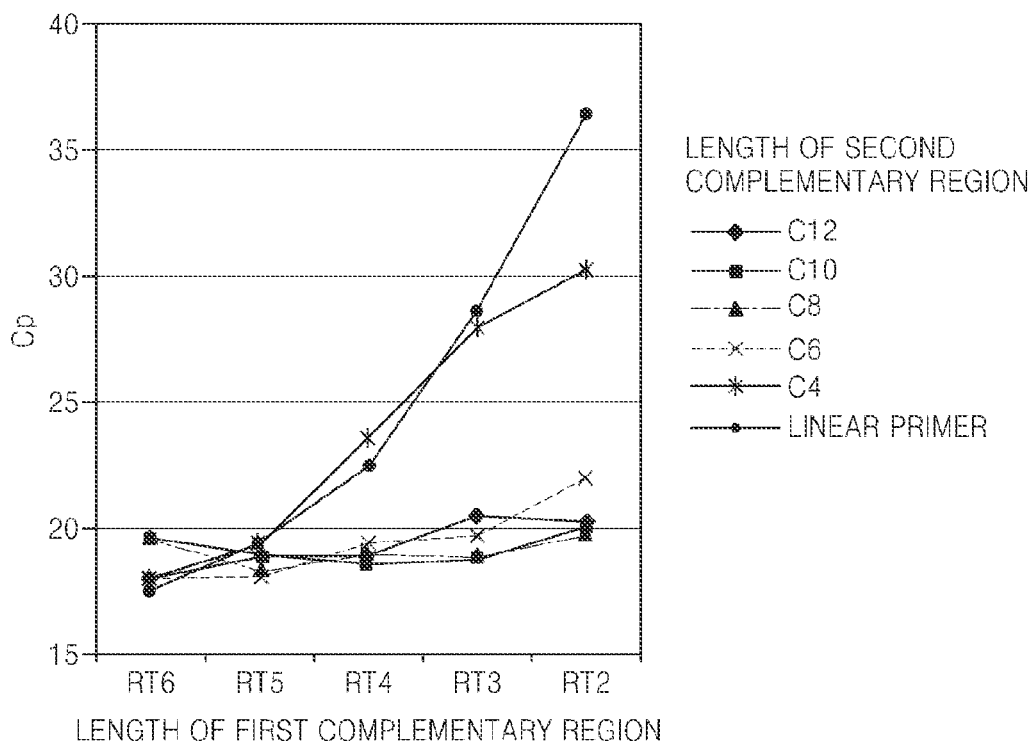
FIG. 3 is a graph illustrating the priming effect of dual-hybridization polynucleotides as a function of the length (number of nucleotides) of a first region complementary to the 3'-terminal region of the miRNA target sequence and the length of a second region complementary to the 5' terminal region of the miRNA target sequence. The length of the first region is shown on the x-axis, Cp value is shown on the y-axis, and the length of the second region is indicated in legend identifying graphing point shapes.

FIG. 3 is a graphical view illustrating priming effect according to the length of the first complementary region and the second complementary region. As shown in FIG. 3, when a sequence that is specific to the 5'-terminal of the target nucleic acid (a second complementary region) is included in an RT primer, the length of the region that is specific to the 3'-terminal of the target nucleic acid (the first complementary region) of the dual-hybridization RT primer can be shortened, while maintaining a low Cp value, as compared to control 3' priming RT ("linear") primer that does not have a second complementary region.

Example 4

Confirmation of the Detection Sensitivity to Target Nucleic Acid miR-210

Detection sensitivity to the target nucleic acid miR-210 performed by the dual-hybridization RT primer and the 3' priming RT primer, respectively, were compared.

Sequences of the target nucleic acid miR-210, 3' priming primer, dual-hybridization RT primer, miRNA-specific PCR primer, and universal PCR primer are shown in Table 3.

TABLE 2

| | RT primer ID | Nucleotide acid sequence |
|---|---|---|
| Dual-hybridization RT primer | C12 RT2 | GTGCAGGGTCCGAGGT AAGACCTCACCG CG (SEQ ID. NO: 65) |
| | C12 RT3 | GTGCAGGGTCCGAGGT AAGACCTCACCG CGC (SEQ ID. NO: 66) |
| | C12 RT4 | GTGCAGGGTCCGAGGT AAGACCTCACCG CGCC (SEQ ID. NO: 67) |
| | C12RT5 | GTGCAGGGTCCGAGGT AAGACCTCACCG CGCCA (SEQ ID. NO: 68) |
| | C12RT6 | GTGCAGGGTCCGAGGT AAGACCTCACCG CGCCAA (SEQ ID. NO: 69) |
| | C10RT2 | GTGCAGGGTCCGAGGT GACCTCACCG CG (SEQ ID. NO: 70) |
| | C10RT3 | GTGCAGGGTCCGAGGT GACCTCACCG CGC (SEQ ID. NO: 71) |
| | C10RT4 | GTGCAGGGTCCGAGGT GACCTCACCG CGCC (SEQ ID. NO: 72) |
| | C10RT5 | GTGCAGGGTCCGAGGT GACCTCACCG CGCCA (SEQ ID. NO: 73) |
| | C10RT6 | GTGCAGGGTCCGAGGT GACCTCACCG CGCCAA (SEQ ID. NO: 74) |
| | C8RT2 | GTGCAGGGTCCGAGGT CCTCACCG CG (SEQ ID. NO: 75) |
| | C8RT3 | GTGCAGGGTCCGAGGT CCTCACCG CGC (SEQ ID. NO: 76) |
| | C8RT4 | GTGCAGGGTCCGAGGT CCTCACCG CGCC (SEQ ID. NO: 77) |
| | C8RT5 | GTGCAGGGTCCGAGGT CCTCACCG CGCCA (SEQ ID. NO: 78) |
| | C8RT6 | GTGCAGGGTCCGAGGT CCTCACCG CGCCAA (SEQ ID. NO: 79) |
| | C6RT2 | GTGCAGGGTCCGAGGT TCACCG CG (SEQ ID. NO: 80) |
| | C6RT3 | GTGCAGGGTCCGAGGT TCACCG CGC (SEQ ID. NO: 81) |
| | C6RT4 | GTGCAGGGTCCGAGGT TCACCG CGCC (SEQ ID. NO: 82) |
| | C6RT5 | GTGCAGGGTCCGAGGT TCACCG CGCCA (SEQ ID. NO: 83) |
| | C6RT6 | GTGCAGGGTCCGAGGT TCACCG CGCCAA (SEQ ID. NO: 84) |
| | C4RT2 | GTGCAGGGTCCGAGGT ACCG CG (SEQ ID. NO: 85) |
| | C4RT3 | GTGCAGGGTCCGAGGT ACCG CGC (SEQ ID. NO: 86) |
| | C4RT4 | GTGCAGGGTCCGAGGT ACCG CGCC (SEQ ID. NO: 87) |
| | C4RT5 | GTGCAGGGTCCGAGGT ACCG CGCCA (SEQ ID. NO: 88) |
| | C4RT6 | GTGCAGGGTCCGAGGT ACCG CGCCAA (SEQ ID. NO: 89) |
| 3' priming RT primer | Linear RT2 | GTGCAGGGTCCGAGGT CG (SEQ ID. NO: 90) |
| | Linear RT3 | GTGCAGGGTCCGAGGT CGC (SEQ ID. NO: 91) |
| | Linear RT4 | GTGCAGGGTCCGAGGT CGCC (SEQ ID. NO: 92) |
| | Linear RT5 | GTGCAGGGTCCGAGGT CGCCA (SEQ ID. NO: 93) |
| | Linear RT6 | GTGCAGGGTCCGAGGT CGCCAA (SEQ ID. NO: 94) |

TABLE 3

| | Nucleotide acid sequence |
|---|---|
| miRNA-210 | 5'-CUGUGCGUGUGACAGCGGCUGA-3' (SEQ ID. NO: 95) |
| Dual-hybridization RT primer | 5'-CGGTGAGGTCTTTGGTTCAT ACGCACAG TCAGC-3' (SEQ ID. NO: 96) |
| 3' priming RT primer | 5'-CGGTGAGGTCTTTGGTTCATTCAGCC-3' (SEQ ID. NO: 97) |
| 3'-terminal PCR primer | 5'-CGCTGGAATGTAAGGAAGT-3' (SEQ ID. NO: 98) |
| 5'-terminal PCR primer | 5'-GTGCGTGTGACAGCGG-3' (SEQ ID. NO: 99) |
| Universal PCR primer | 5'-CGGTGAGGTCTTTGGTTCAT-3' (SEQ ID. NO: 100) |

Detection of the target nucleic acid by the dual-hybridization RT primer was confirmed according to the qPCR method of Example 2.

Figure 4:
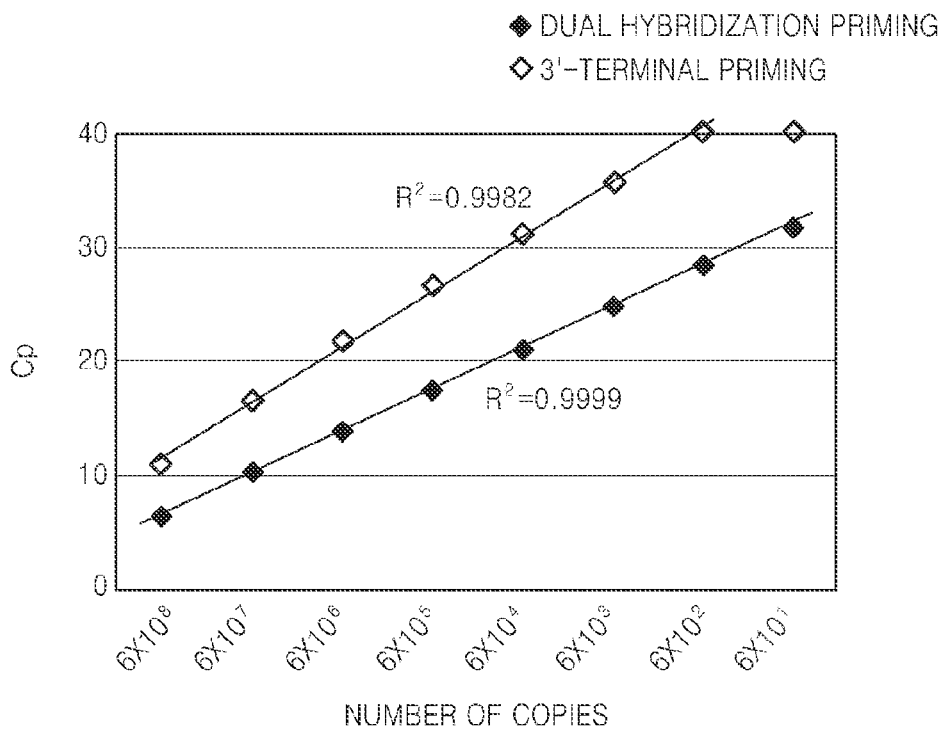
FIG. 4 is a graph illustrating the RT-qPCR detection sensitivity of a dual-hybridization polynucleotide according to an embodiment of the present invention relative to the detection sensitivity of a control 3'-terminal primer; the initial number of copies of miRNA target sequence is shown on x-axis and the Cp value is shown on the y-axis.

FIG. 4 is a graphical view illustrating the detection sensitivity of the dual-hybridization RT primer (♦) as compared to a control 3' priming RT primer (◊) without a second complementary region. As shown in FIG. 4, when the dual-hybridization RT primer was used, Cp values were significantly decreased as compared to the 3' priming RT primer.

Example 5

Confirmation of the Detection Sensitivity to Target Nucleic Acids Target Nucleic Acid miR-16, miR-21, and miR-206

Detection sensitivity to the target nucleic acids miR-16, miR-21, and miR-206, each performed by the dual-hybridization RT primer, were compared.

Sequences of the target nucleic acids miR-16, miR-21, and miR-206, dual-hybridization RT primer, miRNA-specific PCR prime, and universal PCR primer are shown in Table 4.

Detection of the target nucleic acid by the dual-hybridization RT primer was confirmed according to the qPCR method of Example 2.

Figure 5A:
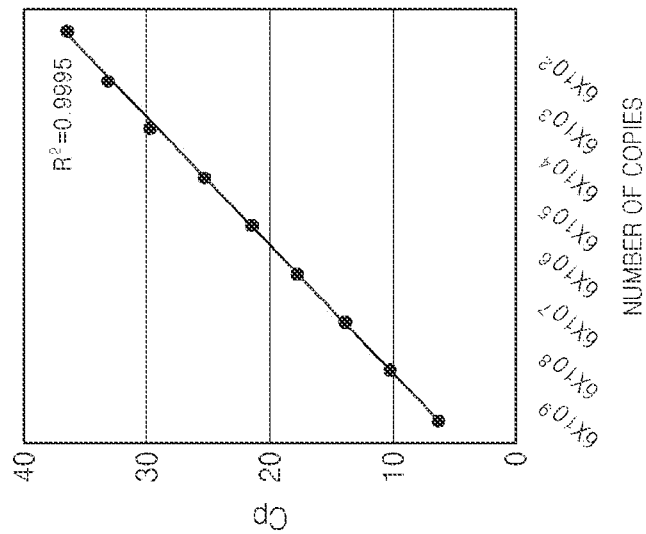
FIG. 5 includes three panels (FIGS. 5A, 5B, and 5C), each of which is a graph illustrating the RT-qPCR detection sensitivity of dual-hybridization polynucleotides according to the invention for the following microRNA target nucleic acids: miR-16 (FIG. 5A), miR-21 (FIG. 5B), and miR-206 (FIG. 5C); the initial number of copies of each miRNA target sequence is shown on the x-axis and the Cp value for PCR product is shown on the y-axis.
Figure 5B:
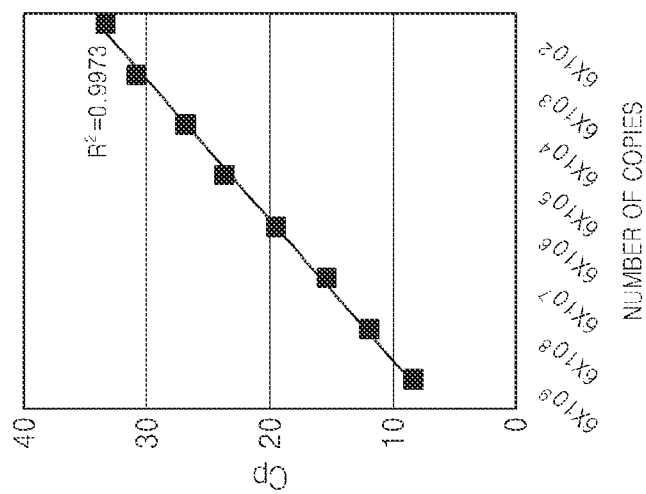
Figure 5C:
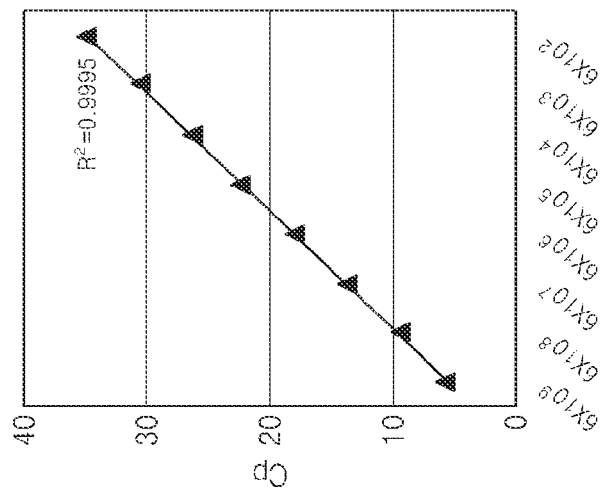

FIGS. 5A, 5B, and 5C are graphical views illustrating the detection sensitivities of dual-hybridization RT primers for target nucleic acid miR-16, miR-21, and miR-206, respectively. As shown in FIGS. 5A through 5C, when the dual-hybridization RT primer was used, Cp values were significantly low. The results also show that dual-hybridization RT primers can detect miRNA templates in a sample having an initial template copy number (before RT-PCR) on the order of $10^{-2}$ or more, $10^{-3}$ or more, $10^{-4}$ or more, $10^{-5}$ or more, $10^{-6}$ or more, $10^{-7}$ or more, $10^{-8}$ or more, or $10^{-9}$ or more.

Example 6

Confirmation of Detection Specificity to Target Nucleic Acids miR-16 and miR-210

Detection specificities of dual-hybridization RT primers to the target nucleic acids miR-16 and miR-210, were confirmed.

Sequences of the target nucleic acids miR-16 and miR-210, variants of miR-16 and variants of miR210, dual-

TABLE 4

| | | Nucleotide acid sequence |
|---|---|---|
| Detection of miR-16 | miR-16 | 5'-UAGCAGCACGUAAAUAUUGGCG-3' (SEQ ID. NO: 101) |
| | Dual-hybridization RT primer | 5'-GTGCAGGGTCCGAGGTGCTACGCC-3' (SEQ ID. NO: 102) |
| | miR-16-specific PCR primer | 5'-CGCGCTAGCAGCACGTAAAT-3' (SEQ ID. NO: 103) |
| | Universal PCR primer | 5'-GTGCAGGGTCCGAGGT-3' (SEQ ID. NO: 104) |
| Detection of miR-21 | miR-21 | 5'-UAGCUUAUCAGACUGAUGUUGA-3' (SEQ ID. NO: 105) |
| | Dual-hybridization RT primer | 5'-CGGTGAGGTCTTTGGTTCATaagctatcaac-3' (SEQ ID. NO: 106) |
| | miR-21-specific PCR primer | 5'-CGGTAGCTTATCAGACTGATGT-3' (SEQ ID. NO: 107) |
| | Universal PCR primer | 5'-CGGTGAGGTCTTTGGTTCAT-3' (SEQ ID. NO: 108) |
| Detection of miR-206 | miR-206 | 5'-UGGAAUGUAAGGAAGUGUGUGG-3' (SEQ ID. NO: 109) |
| | Dual-hybridization RT primer | 5'-CGGTGAGGTCTTTGGTTCATATTCCACCAC-3' (SEQ ID. NO: 110) |
| | miR-206-specific PCR primer | 5'-CGCTGGAATGTAAGGAAGT-3' (SEQ ID. NO: 111) |
| | Universal PCR primer | 5'-CGGTGAGGTCTTTGGTTCAT-3' (SEQ ID. NO: 112) | hybridization RT primers, control 3' priming primers, miRNA-specific PCR primer, and universal PCR primer are shown in Table 5. Bold letters in variant nucleic acid sequences represent the substituted nucleic acid. For example, miR16-M1A indicates that the first nucleic acid from the 5'-terminal of miR16 is replaced with adenosine (A).

and 6B show the change in Cp value obtained by the following process: (1) determining Cp values obtained when using the dual-hybridization primer and the 3' priming primer shown in Table 5 to detect miR-16 and miR-210, (2) determining Cp values using the same dual-hybridization primers and the same 3' priming primers to detect each target nucleic acid variant indicated on the x-axis of FIG. 6A or 6B,

TABLE 5

| | | Nucleotide acid sequence |
|---|---|---|
| Detection of miR-16 | miR-16 | 5'-UAGCAGCACGUAAAUAUUGGCG-3' (SEQ ID. NO: 113) |
| | miR16-M1A (variant) | 5'-AAGCAGCACGUAAAUAUUGGCG-3' (SEQ ID. NO: 114) |
| | miR16-M2U (variant) | 5'-UUGCAGCACGUAAAUAUUGGCG-3' (SEQ ID. NO: 115) |
| | miR16-M3U (variant) | 5'-UAUCAGCACGUAAAUAUUGGCG-3' (SEQ ID. NO: 116) |
| | miR16-M4A (variant) | 5'-UAGAAGCACGUAAAUAUUGGCG-3' (SEQ ID. NO: 117) |
| | miR16-M19U (variant) | 5'-UAGCAGCACGUAAAUAUUUGCG-3' (SEQ ID. NO: 118) |
| | miR16-M20C (variant) | 5'-UAGCAGCACGUAAAUAUUGCCG-3' (SEQ ID. NO: 119) |
| | miR16-M21A (variant) | 5'-UAGCAGCACGUAAAUAUUGGAG-3' (SEQ ID. NO: 120) |
| | miR16-M22U (variant) | 5'-UAGCAGCACGUAAAUAUUGGCU-3' (SEQ ID. NO: 121) |
| | Dual-hybridization RT primer | 5'-GTGCAGGGTCCGAGGTGCTACGCC-3' (SEQ ID. NO: 122) |
| | 3' priming primer | 5'-GTGCAGGGTCCGAGGTCGCCAA-3' (SEQ ID. NO: 123) |
| | miR-16-specific PCR primer | 5'-CGCGCTAGCAGCACGTAAAT-3' (SEQ ID. NO: 124) |
| | Universal PCR primer | 5'-GTGCAGGGTCCGAGGT-3' (SEQ ID. NO: 125) |
| Detection of miR-210 | miR-210 | 5'-UAGCUUAUCAGACUGAUGUUGA-3' (SEQ ID. NO: 126) |
| | miR-210-M1A (variant) | 5'-AUGUGCGUGUGACAGCGGCUGA-3' (SEQ ID. NO: 127) |
| | miR-210-M2A (variant) | 5'-CAGUGCGUGUGACAGCGGCUGA-3' (SEQ ID. NO: 128) |
| | miR-210-M3A (variant) | 5'-CUAUGCGUGUGACAGCGGCUGA-3' (SEQ ID. NO: 129) |
| | miR-210-M4C (variant) | 5'-CUGCGCGUGUGACAGCGGCUGA-3' (SEQ ID. NO: 130) |
| | miR-210-M6A (variant) | 5'-CUGUGAGUGUGACAGCGGCUGA-3' (SEQ ID. NO: 131) |
| | miR-210-M19U (variant) | 5'-CUGUGCGUGUGACAGCGGUUGA-3' (SEQ ID. NO: 132) |
| | miR-210-M20G (variant) | 5'-CUGUGCGUGUGACAGCGGCGGA-3' (SEQ ID. NO: 133) |
| | miR-210-M21A (variant) | 5'-CUGUGCGUGUGACAGCGGCUAA-3' (SEQ ID. NO: 134) |
| | miR-210-M22G (variant) | 5'-CUGUGCGUGUGACAGCGGCUGG-3' (SEQ ID. NO: 135) |
| | Dual-hybridization RT primer | 5'-CCGGTGAGGTCTTTGGTTCATACGCACAGTCAGC-3' (SEQ ID. NO: 136) |
| | 3' priming primer | 5'-CGGTGAGGTCTTTGGTTCATTCAGCC-3' (SEQ ID. NO: 137) |
| | miR-210-specific PCR primer | 5'-CTGTGCGTGTGACAGC-3' (SEQ ID. NO: 138) |
| | Universal PCR primer | 5'-CGGTGAGGTCTTTGGTTCAT-3' (SEQ ID. NO: 139) |

Detection of target nucleic acids, including variants with substituted nucleic acid sequences, by the dual-hybridization RT primer and by control 3' priming RT primer was confirmed according to the qPCR method of Example 2.

Figure 6A:
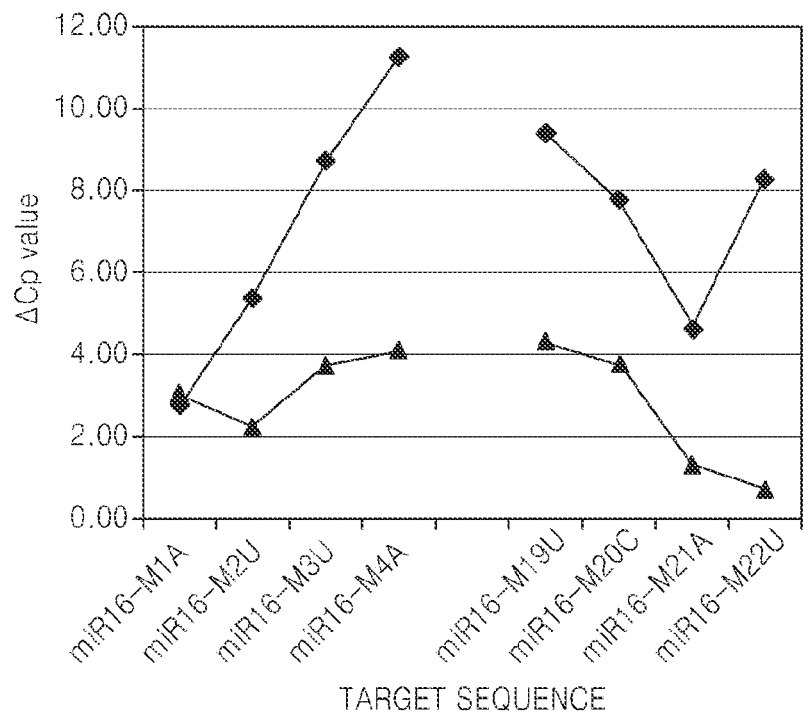
FIG. 6 includes two panels (FIGS. 6A and 6B), each of which is a graph illustrating the RT-qPCR detection specificity of dual-hybridization polynucleotides according to the invention (indicated by ♦) as compared to the specificity of control 3'-terminal primers (indicated by ▲) for microRNA target nucleic acids miR-16 (FIG. 6A) and miR-210 (FIG. 6B).
Figure 6B:
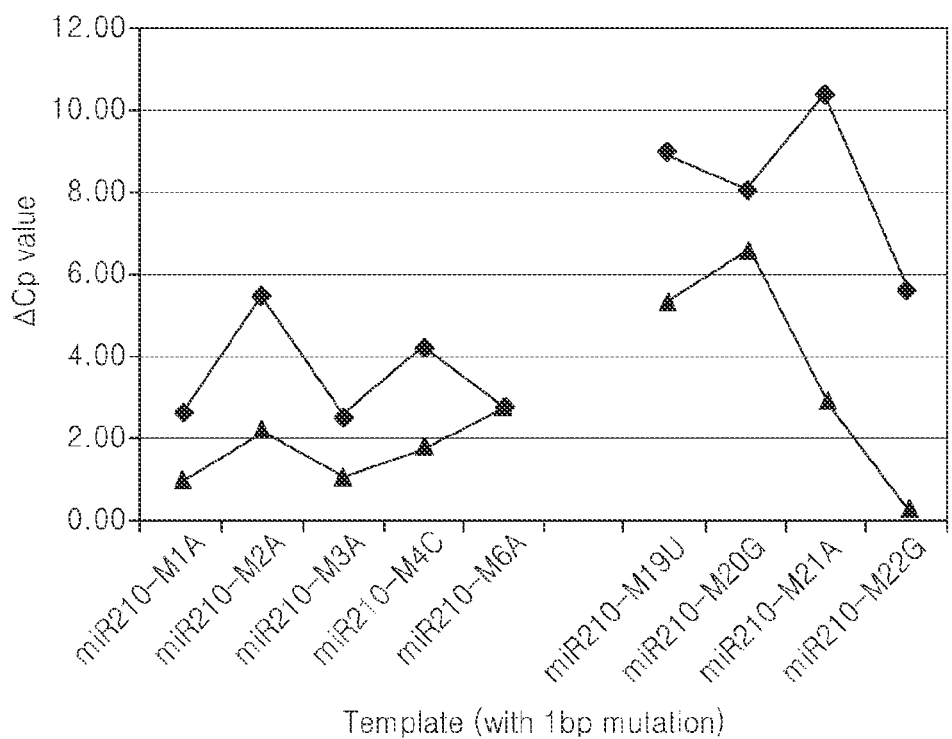

FIGS. 6A and 6B are graphical views illustrating specificities for detecting target nucleic acids miR-16 and miR-210, respectively, by dual-hybridization primers (♦) and by 3'-terminal primer (▲). Specifically, FIGS. 6A and (3) determining the difference in Cp values (ΔCp) for each target nucleic acid and variant. In FIG. 6A, y-axis indicates ΔCp=(Cp value for miR-16 variant)−(Cp value for miR-16). In FIG. 6B, y-axis indicates ΔCp=(Cp value for miR-210 variant)−(CP value for each miR-210). As shown in FIGS. 6A and 6B, the specificity improved with the dual-hybridization RT primer as compared to the 3' priming RT primer.

Example 7

Confirmation that Dual-Hybridization RT Primers have Low Cross-Reactivity Among Let-7 Family miRNAs Detection specificity and low cross-reactivity of dual-hybridization RT primers towards Let-7 family miRNA target sequences was confirmed.

Sequences of the Let-7 miRNA target nucleic acids, dual-hybridization RT primer, and miRNA-specific PCR primer are shown in Table 6. Bold letters of the nucleic acid sequences represent the substituted nucleotides in target nucleic acid sequences relative to let-7a sequence.

TABLE 6

| | | Nucleotide sequence |
|---|---|---|
| Sequence of target | let-7a | 5'-UGAGGUAGUAGGUUGUAUAGUU-3' (SEQ ID. NO: 140) |
| | let-7b | 5'-UGAGGUAGUAGGUUGUGUGGUU-3' (SEQ ID. NO: 141) |
| | let-7c | 5'-UGAGGUAGUAGGUUGUAUGGUU-3' (SEQ ID. NO: 142) |
| | let-7d | 5'-AGAGGUAGUAGGUUGCAUAGUU-3' (SEQ ID. NO: 143) |
| | let-7e | 5'-UGAGGUAGGAGGUUGUAUAGUU-3' (SEQ ID. NO: 144) |
| Dual-hybridization RT primer | let-7a | 5'-GTGCAGGGTCCGAGGTACCTCAAACT-3' (SEQ ID. NO: 145) |
| | let-7b | 5'-GTGCAGGGTCCGAGGTACCTCAAACC-3' (SEQ ID. NO: 146) |
| | let-7c | 5'-GTGCAGGGTCCGAGGTACCTCAAACC-3' (SEQ ID. NO: 147) |
| | let-7d | 5'-GTGCAGGGTCCGAGGTACCTCTAACT-3' (SEQ ID. NO: 148) |
| | let-7e | 5'-GTGCAGGGTCCGAGGTACCTCAAACT-3' (SEQ ID. NO: 149) |
| miRNA-specific PCR primer | let-7a | 5'-GCCGCTGAGGTAGTAGGTTGTA-3' (SEQ ID. NO: 150) |
| | let-7b-1 | 5'-CGCTGAGGTAGTAGGTTGTG-3' (SEQ ID. NO: 151) |
| | let-7c | 5'-GCCGCTGAGGTAGTAGGTTGTA-3' (SEQ ID. NO: 152) |
| | let-7d | 5'-GCCGCAGAGGTAGTAGGTTGC-3' (SEQ ID. NO: 153) |
| | let-7e | 5'-TGCCGGTGAGGTAGGAGG-3' (SEQ ID. NO: 154) |

The cross-reactivity (%) of the dual-hybridization RT primers to different Let-7 family niRNA was confirmed using the qPCR method of Example 2.

TABLE 7

| | let-7a | let-7b | let-7c | let-7d | let-7e |
|---|---|---|---|---|---|
| let-7a | | 0.06 | 1.28 | 0.07 | 0.21 |
| let-7b | 4.07 | | 3.18 | 0.06 | 0.03 |
| let-7c | 1.72 | 0.22 | | 0.06 | 0.03 |
| let-7d | 0.18 | 0.00 | 0.03 | | 0.00 |

Table 7 shows the cross-sensitivity (%) of the dual-hybridization RT primers to different Let-7 family sequences. As shown in Table 7, the cross-sensitivity of the dual-hybridization RT primers was found to be less than 5%.

As described above, according to the one or more of the above embodiments of the present invention, a dual-hybridization polynucleotide may include a shortened (reduced number of nucleotides in the) first complementary region that binds to the 3'-terminal of a target nucleic acid and may be used to amplify the target nucleic acid with excellent sensitivity and/or specificity. Compositions and kits including the dual-hybridization polynucleotide may be used to amplify and thereby detect the target nucleic acid with excellent sensitivity and/or specificity. The methods of producing a nucleotide sequence complementary to the target nucleic acid may be used to amplify or detect the target nucleotide sequence with excellent sensitivity and/or specificity.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of producing a nucleotide sequence complementary to a linear target nucleic acid, the method comprising consisting essentially of:
   hybridizing a linear target nucleic acid with a dual-hybridization polynucleotide to form a hybridized complex of the linear target nucleic acid and the dual-hybridization polynucleotide,
   wherein the dual-hybridization polynucleotide comprises a first complementary region that is complementary to at least two consecutive nucleotides of the 3'-terminus of a linear target nucleic acid, wherein the length of the first complementary region in the dual hybridization polynucleotide is 2 to 4 nucleotides;
   a second complementary region that is complementary to at least two consecutive nucleotides from the 5'-terminus of a linear target nucleic acid, wherein the first complementary region is located 3' of the second complementary region in the dual hybridization polynucleotide, wherein the second complementary region in the dual hybridization polynucleotide comprises nucleotides that are complementary to about 3 to 20 consecutive nucleotides from the 5'-terminal of the linear target nucleic acid; and
   a third region that is not complementary to the linear target nucleic acid and is located 5' of the second complementary region, so that the second complementary region is positioned between the first complementary region and the third region; and
   incubating the hybridized complex of the linear target nucleic acid and dual hybridization polynucleotide in the presence of a nucleic acid polymerase to produce a nucleotide sequence complementary to the linear target nucleic acid by extending the 3'-terminal of the polynucleotide.

2. The method of claim 1, wherein the nucleic acid polymerase has strand displacement activity.

3. The method of claim 2, wherein the nucleic acid polymerase having strand displacement activity is a reverse transcriptase.

4. The method of claim 3, wherein the reverse transcriptase is an HIV transcriptase, MMLV transcriptase, or AMV transcriptase.

5. The method of claim 1, wherein the linear target nucleic acid is RNA.

6. The method of claim 1, wherein the linear target nucleic acid is non-coding RNA, micro RNA (miRNA), small interfering RNA (siRNA), tRNA, or decapped mRNA.

7. The method of claim 1, wherein the second complementary region in the dual-hybridization polynucleotide has a length of 3 to 20 nucleotides.

8. The method of claim 1, wherein the linear target nucleic acid has a length of about 15 to about 200 nucleotides.

9. The method of claim 1, wherein the third region in the dual-hybridization polynucleotide comprises one or more of a primer sequence, a restriction enzyme recognition site, or a probe-binding site.

10. The method of claim 1, wherein at least one of the first complementary region and the second complementary region in the dual-hybridization polynucleotide comprises DNA, RNA, peptide nucleic acid (PNA), locked nucleic acid (LNA), ZIP nucleic acid or nucleotide analogue.

11. The method of claim 1, wherein the third region in the dual-hybridization polynucleotide comprises DNA, RNA, peptide nucleic acid (PNA), locked nucleic acid (LNA), ZIP nucleic acid or nucleotide analogue.

* * * * *

SEQUENCE LISTING

```
<160> NUMBER OF SEQ ID NOS: 154

<210> SEQ ID NO 1
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 1
ugagguagua gguugugugg uu                                                  22

<210> SEQ ID NO 2
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 2
cggtgaggtc tttggttcat aaccac                                              26

<210> SEQ ID NO 3
<211> LENGTH: 32
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 3
cggtgaggtc tttggttcat ctacctcaaa cc                                       32

<210> SEQ ID NO 4
<211> LENGTH: 20
<212> TYPE: DNA
<213> ORGANISM: Artificial Sequence
<220> FEATURE:
<223> OTHER INFORMATION: Synthetic (miRNA specific PCR primer)

<400> SEQUENCE: 4
cgctgaggta gtaggttgtg                                                     20

<210> SEQ ID NO 5
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 5
agagguagua gguugcauag uu                                                  22
```

<210> SEQ ID NO 6
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 6
cggtgaggtc tttggttcat aactat                                      26

<210> SEQ ID NO 7
<211> LENGTH: 32
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 7
cggtgaggtc tttggttcat ctacctctaa ct                               32

<210> SEQ ID NO 8
<211> LENGTH: 19
<212> TYPE: DNA
<213> ORGANISM: Artificial Sequence
<220> FEATURE:
<223> OTHER INFORMATION: Synthetic (miRNA specific PCR primer)

<400> SEQUENCE: 8
cgcagaggta gtaggttgc                                              19

<210> SEQ ID NO 9
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 9
aacccguaga uccgaacuug ug                                          22

<210> SEQ ID NO 10
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 10
cggtgaggtc tttggttcat cacaag                                      26

<210> SEQ ID NO 11
<211> LENGTH: 30
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 11
cggtgaggtc tttggttcat cgggttcaca                                  30

<210> SEQ ID NO 12
<211> LENGTH: 17

```
<212> TYPE: DNA
<213> ORGANISM: Artificial Sequence
<220> FEATURE:
<223> OTHER INFORMATION: Synthetic (miRNA specific PCR primer)

<400> SEQUENCE: 12
caacccgtag atccgaa                                                   17

<210> SEQ ID NO 13
<211> LENGTH: 23
<212> TYPE: RNA
<213> ORGANISM: Artificial Sequence
<220> FEATURE:
<223> OTHER INFORMATION: Synthetic (microRNA)

<400> SEQUENCE: 13
uacccguuag auccgaauuu gug                                            23

<210> SEQ ID NO 14
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 14
cggtgaggtc tttggttcat cacaaa                                         26

<210> SEQ ID NO 15
<211> LENGTH: 30
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 15
cggtgaggtc tttggttcat agggtacaca                                     30

<210> SEQ ID NO 16
<211> LENGTH: 19
<212> TYPE: DNA
<213> ORGANISM: Artificial Sequence
<220> FEATURE:
<223> OTHER INFORMATION: Synthetic (miRNA specific PCR primer)

<400> SEQUENCE: 16
cgtaccctgt agatccgaa                                                 19

<210> SEQ ID NO 17
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 17
uggaguguga caaugguguu ug                                             22

<210> SEQ ID NO 18
<211> LENGTH: 26
<212> TYPE: DNA
<213> ORGANISM: Artificial Sequence
<220> FEATURE:
<223> OTHER INFORMATION: Synthetic (3' priming reverse transcription
      primer)
```

<400> SEQUENCE: 18
cggtgaggtc tttggttcat caaaca                                    26

<210> SEQ ID NO 19
<211> LENGTH: 32
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 19
cggtgaggtc tttggttcat acactccaca aa                             32

<210> SEQ ID NO 20
<211> LENGTH: 18
<212> TYPE: DNA
<213> ORGANISM: Artificial Sequence
<220> FEATURE:
<223> OTHER INFORMATION: Synthetic (miRNA specific PCR primer)

<400> SEQUENCE: 20
cgtggagtgt gacaatgg                                             18

<210> SEQ ID NO 21
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 21
ucccugagac ccuaacuugu ga                                        22

<210> SEQ ID NO 22
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 22
cggtgaggtc tttggttcat tcacaa                                    26

<210> SEQ ID NO 23
<211> LENGTH: 32
<212> TYPE: DNA
<213> ORGANISM: Artificial Sequence
<220> FEATURE:
<223> OTHER INFORMATION: Sythetic (Dual hybridization reverse
      transcription primer)

<400> SEQUENCE: 23
cggtgaggtc tttggttcat ctcagggatc ac                             32

<210> SEQ ID NO 24
<211> LENGTH: 18
<212> TYPE: DNA
<213> ORGANISM: Artificial Sequence
<220> FEATURE:
<223> OTHER INFORMATION: Synthetic (miRNA specific PCR primer)

<400> SEQUENCE: 24
cgtccctgag accctaac                                             18

```
<210> SEQ ID NO 25
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 25
cagugcaaug uuaaaagggc au                                              22

<210> SEQ ID NO 26
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 26
cggtgaggtc tttggttcat atgccc                                          26

<210> SEQ ID NO 27
<211> LENGTH: 30
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 27
cggtgaggtc tttggttcat gcactgatgc                                      30

<210> SEQ ID NO 28
<211> LENGTH: 18
<212> TYPE: DNA
<213> ORGANISM: Artificial Sequence
<220> FEATURE:
<223> OTHER INFORMATION: Synthetic (miRNA specific PCR primer)

<400> SEQUENCE: 28
gcgcagtgca atgttaaa                                                   18

<210> SEQ ID NO 29
<211> LENGTH: 23
<212> TYPE: RNA
<213> ORGANISM: Artificial Sequence
<220> FEATURE:
<223> OTHER INFORMATION: Synthetic (microRNA)

<400> SEQUENCE: 29
uauggcuuuu uauuccuaug uga                                             23

<210> SEQ ID NO 30
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 30
cggtgaggtc tttggttcat tcacat                                          26

<210> SEQ ID NO 31
<211> LENGTH: 32
```

```
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 31
cggtgaggtc tttggttcat aagccatatc ac                                      32

<210> SEQ ID NO 32
<211> LENGTH: 20
<212> TYPE: DNA
<213> ORGANISM: Artificial Sequence
<220> FEATURE:
<223> OTHER INFORMATION: Synthetic (miRNA specific PCR primer)

<400> SEQUENCE: 32
cgctatggct ttttattcct                                                    20

<210> SEQ ID NO 33
<211> LENGTH: 23
<212> TYPE: RNA
<213> ORGANISM: Artificial Sequence
<220> FEATURE:
<223> OTHER INFORMATION: Synthetic (microRNA)

<400> SEQUENCE: 33
uauggcuuuu cauuccuaug uga                                                23

<210> SEQ ID NO 34
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 34
cggtgaggtc tttggttcat tcacat                                             26

<210> SEQ ID NO 35
<211> LENGTH: 30
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 35
cggtgaggtc tttggttcat gccatatcac                                         30

<210> SEQ ID NO 36
<211> LENGTH: 19
<212> TYPE: DNA
<213> ORGANISM: Artificial Sequence
<220> FEATURE:
<223> OTHER INFORMATION: Synthetic (miRNA specific PCR primer)

<400> SEQUENCE: 36
cgtatggctt ttcattcct                                                     19

<210> SEQ ID NO 37
<211> LENGTH: 22
<212> TYPE: RNA
<213> ORGANISM: Artificial Sequence
<220> FEATURE:
<223> OTHER INFORMATION: Synthetic (microRNA)
```

<400> SEQUENCE: 37
uagcagcaca ucaugguuua ca                                              22

<210> SEQ ID NO 38
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 38
cggtgaggtc tttggttcat tgtaaa                                          26

<210> SEQ ID NO 39
<211> LENGTH: 30
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 39
cggtgaggtc tttggttcat ctgctatgta                                      30

<210> SEQ ID NO 40
<211> LENGTH: 18
<212> TYPE: DNA
<213> ORGANISM: Artificial Sequence
<220> FEATURE:
<223> OTHER INFORMATION: Synthetic (miRNA specific PCR primer)

<400> SEQUENCE: 40
cgtagcagca catcatgg                                                   18

<210> SEQ ID NO 41
<211> LENGTH: 23
<212> TYPE: RNA
<213> ORGANISM: Artificial Sequence
<220> FEATURE:
<223> OTHER INFORMATION: Synthetic (microRNA)

<400> SEQUENCE: 41
uaaagugcuu auagugcagg uag                                             23

<210> SEQ ID NO 42
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 42
cggtgaggtc tttggttcat ctacct                                          26

<210> SEQ ID NO 43
<211> LENGTH: 32
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 43
cggtgaggtc tttggttcat gcactttact ac                          32

<210> SEQ ID NO 44
<211> LENGTH: 21
<212> TYPE: DNA
<213> ORGANISM: Artificial Sequence
<220> FEATURE:
<223> OTHER INFORMATION: Synthetic (miRNA specific PCR primer)

<400> SEQUENCE: 44
ccgctaaagt gcttatagtg c                                      21

<210> SEQ ID NO 45
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 45
acagcaggca cagacaggca gu                                     22

<210> SEQ ID NO 46
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 46
cggtgaggtc tttggttcat actgcc                                 26

<210> SEQ ID NO 47
<211> LENGTH: 32
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 47
cggtgaggtc tttggttcat cctgctgtac tg                          32

<210> SEQ ID NO 48
<211> LENGTH: 17
<212> TYPE: DNA
<213> ORGANISM: Artificial Sequence
<220> FEATURE:
<223> OTHER INFORMATION: Synthetic (miRNA specific PCR primer)

<400> SEQUENCE: 48
cacagcaggc acagaca                                           17

<210> SEQ ID NO 49
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 49
uagcaccauc ugaaaucggu ua                                     22

<210> SEQ ID NO 50
<211> LENGTH: 26

```
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 50
cggtgaggtc tttggttcat taaccg                                          26

<210> SEQ ID NO 51
<211> LENGTH: 32
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 51
cggtgaggtc tttggttcat tggtgctata ac                                   32

<210> SEQ ID NO 52
<211> LENGTH: 19
<212> TYPE: DNA
<213> ORGANISM: Artificial Sequence
<220> FEATURE:
<223> OTHER INFORMATION: Synthetic (miRNA specific PCR primer)

<400> SEQUENCE: 52
cgctagcacc atctgaaat                                                  19

<210> SEQ ID NO 53
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 53
uggcaguguc uuagcugguu gu                                              22

<210> SEQ ID NO 54
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 54
cggtgaggtc tttggttcat acaacc                                          26

<210> SEQ ID NO 55
<211> LENGTH: 32
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 55
cggtgaggtc tttggttcat cactgccaac aa                                   32

<210> SEQ ID NO 56
<211> LENGTH: 18
<212> TYPE: DNA
<213> ORGANISM: Artificial Sequence
<220> FEATURE:
```

```
<223> OTHER INFORMATION: Synthetic (miRNA specific PCR primer)

<400> SEQUENCE: 56
gcctggcagt gtcttagc                                                 18

<210> SEQ ID NO 57
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 57
aucgugcauc cuuuuagagu gu                                            22

<210> SEQ ID NO 58
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 58
cggtgaggtc tttggttcat acactc                                        26

<210> SEQ ID NO 59
<211> LENGTH: 32
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 59
cggtgaggtc tttggttcat tgcacgatac ac                                 32

<210> SEQ ID NO 60
<211> LENGTH: 18
<212> TYPE: DNA
<213> ORGANISM: Artificial Sequence
<220> FEATURE:
<223> OTHER INFORMATION: Synthetic (miRNA specific PCR primer)

<400> SEQUENCE: 60
cgatcgtgca tcctttta                                                 18

<210> SEQ ID NO 61
<211> LENGTH: 20
<212> TYPE: DNA
<213> ORGANISM: Artificial Sequence
<220> FEATURE:
<223> OTHER INFORMATION: Synthetic (universal PCR primer)

<400> SEQUENCE: 61
cggtgaggtc tttggttcat                                               20

<210> SEQ ID NO 62
<211> LENGTH: 42
<212> TYPE: RNA
<213> ORGANISM: Artificial Sequence
<220> FEATURE:
<223> OTHER INFORMATION: Synthetic (microRNA)

<400> SEQUENCE: 62
cggugagguc uuugguucau uagcagcacg uaaauauugg cg                      42
```

<210> SEQ ID NO 63
<211> LENGTH: 20
<212> TYPE: DNA
<213> ORGANISM: Artificial Sequence
<220> FEATURE:
<223> OTHER INFORMATION: Synthetic (miRNA specific PCR primer)

<400> SEQUENCE: 63
cgcgctagca gcacgtaaat                                             20

<210> SEQ ID NO 64
<211> LENGTH: 16
<212> TYPE: DNA
<213> ORGANISM: Artificial Sequence
<220> FEATURE:
<223> OTHER INFORMATION: Synthetic (universal PCR primer)

<400> SEQUENCE: 64
gtgcagggtc cgaggt                                                 16

<210> SEQ ID NO 65
<211> LENGTH: 30
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 65
gtgcagggtc cgaggtaaga cctcaccgcg                                  30

<210> SEQ ID NO 66
<211> LENGTH: 31
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 66
gtgcagggtc cgaggtaaga cctcaccgcg c                                31

<210> SEQ ID NO 67
<211> LENGTH: 32
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 67
gtgcagggtc cgaggtaaga cctcaccgcg cc                               32

<210> SEQ ID NO 68
<211> LENGTH: 33
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 68
gtgcagggtc cgaggtaaga cctcaccgcg cca                              33

<210> SEQ ID NO 69

```
<211> LENGTH: 34
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 69
gtgcagggtc cgaggtaaga cctcaccgcg ccaa                             34

<210> SEQ ID NO 70
<211> LENGTH: 28
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 70
gtgcagggtc cgaggtgacc tcaccgcg                                    28

<210> SEQ ID NO 71
<211> LENGTH: 29
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 71
gtgcagggtc cgaggtgacc tcaccgcgc                                   29

<210> SEQ ID NO 72
<211> LENGTH: 30
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 72
gtgcagggtc cgaggtgacc tcaccgcgcc                                  30

<210> SEQ ID NO 73
<211> LENGTH: 31
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 73
gtgcagggtc cgaggtgacc tcaccgcgcc a                                31

<210> SEQ ID NO 74
<211> LENGTH: 32
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 74
gtgcagggtc cgaggtgacc tcaccgcgcc aa                               32

<210> SEQ ID NO 75
<211> LENGTH: 26
```

```
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 75
gtgcagggtc cgaggtcctc accgcg                                          26

<210> SEQ ID NO 76
<211> LENGTH: 27
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 76
gtgcagggtc cgaggtcctc accgcgc                                         27

<210> SEQ ID NO 77
<211> LENGTH: 28
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 77
gtgcagggtc cgaggtcctc accgcgcc                                        28

<210> SEQ ID NO 78
<211> LENGTH: 29
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 78
gtgcagggtc cgaggtcctc accgcgcca                                       29

<210> SEQ ID NO 79
<211> LENGTH: 30
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 79
gtgcagggtc cgaggtcctc accgcgccaa                                      30

<210> SEQ ID NO 80
<211> LENGTH: 24
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 80
gtgcagggtc cgaggttcac cgcg                                            24

<210> SEQ ID NO 81
<211> LENGTH: 25
<212> TYPE: DNA
```

-continued

<213> ORGANISM: Artificial Sequence
<220> FEATURE:
<223> OTHER INFORMATION: Synthetic (Dual hybridization reverse
      transcription primer)

<400> SEQUENCE: 81
gtgcagggtc cgaggttcac cgcgc                                    25

<210> SEQ ID NO 82
<211> LENGTH: 26
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 82
gtgcagggtc cgaggttcac cgcgcc                                   26

<210> SEQ ID NO 83
<211> LENGTH: 27
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 83
gtgcagggtc cgaggttcac cgcgcca                                  27

<210> SEQ ID NO 84
<211> LENGTH: 28
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 84
gtgcagggtc cgaggttcac cgcgccaa                                 28

<210> SEQ ID NO 85
<211> LENGTH: 22
<212> TYPE: DNA
<213> ORGANISM: Artificial Sequence
<220> FEATURE:
<223> OTHER INFORMATION: Synthertic (Dual hybridization reverse
      transcription primer)

<400> SEQUENCE: 85
gtgcagggtc cgaggtaccg cg                                       22

<210> SEQ ID NO 86
<211> LENGTH: 23
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 86
gtgcagggtc cgaggtaccg cgc                                      23

<210> SEQ ID NO 87
<211> LENGTH: 24
<212> TYPE: DNA
<213> ORGANISM: Artificial Sequence

```
<220> FEATURE:
<223> OTHER INFORMATION: Synthetic (Dual hybridization reverse
      transcription primer)

<400> SEQUENCE: 87
gtgcagggtc cgaggtaccg cgcc                                          24

<210> SEQ ID NO 88
<211> LENGTH: 25
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 88
gtgcagggtc cgaggtaccg cgcca                                         25

<210> SEQ ID NO 89
<211> LENGTH: 26
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 89
gtgcagggtc cgaggtaccg cgccaa                                        26

<210> SEQ ID NO 90
<211> LENGTH: 18
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 90
gtgcagggtc cgaggtcg                                                 18

<210> SEQ ID NO 91
<211> LENGTH: 19
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 91
gtgcagggtc cgaggtcgc                                                19

<210> SEQ ID NO 92
<211> LENGTH: 20
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 92
gtgcagggtc cgaggtcgcc                                               20

<210> SEQ ID NO 93
<211> LENGTH: 21
<212> TYPE: DNA
<213> ORGANISM: Artificial Sequence
<220> FEATURE:
```

<223> OTHER INFORMATION: Synthetic (3' priming reverse transcription
      primer)

<400> SEQUENCE: 93
gtgcagggtc cgaggtcgcc a                                              21

<210> SEQ ID NO 94
<211> LENGTH: 22
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 94
gtgcagggtc cgaggtcgcc aa                                             22

<210> SEQ ID NO 95
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 95
cugugcgugu gacagcggcu ga                                             22

<210> SEQ ID NO 96
<211> LENGTH: 33
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 96
cggtgaggtc tttggttcat acgcacagtc agc                                 33

<210> SEQ ID NO 97
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 97
cggtgaggtc tttggttcat tcagcc                                         26

<210> SEQ ID NO 98
<211> LENGTH: 19
<212> TYPE: DNA
<213> ORGANISM: Artificial Sequence
<220> FEATURE:
<223> OTHER INFORMATION: Synthetic (3' end PCR primer)

<400> SEQUENCE: 98
cgctggaatg taaggaagt                                                 19

<210> SEQ ID NO 99
<211> LENGTH: 16
<212> TYPE: DNA
<213> ORGANISM: Artificial Sequence
<220> FEATURE:
<223> OTHER INFORMATION: Synthetic (5' end PCR primer)

<400> SEQUENCE: 99
gtgcgtgtga cagcgg                                                                          16

<210> SEQ ID NO 100
<211> LENGTH: 20
<212> TYPE: DNA
<213> ORGANISM: Artificial Sequence
<220> FEATURE:
<223> OTHER INFORMATION: Synthetic (universal PCR primer)

<400> SEQUENCE: 100
cggtgaggtc tttggttcat                                                                      20

<210> SEQ ID NO 101
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 101
uagcagcacg uaaauauugg cg                                                                   22

<210> SEQ ID NO 102
<211> LENGTH: 24
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 102
gtgcagggtc cgaggtgcta cgcc                                                                 24

<210> SEQ ID NO 103
<211> LENGTH: 20
<212> TYPE: DNA
<213> ORGANISM: Artificial Sequence
<220> FEATURE:
<223> OTHER INFORMATION: Synthetic (miRNA specific PCR primer)

<400> SEQUENCE: 103
cgcgctagca gcacgtaaat                                                                      20

<210> SEQ ID NO 104
<211> LENGTH: 16
<212> TYPE: DNA
<213> ORGANISM: Artificial Sequence
<220> FEATURE:
<223> OTHER INFORMATION: Synthetic (universal PCR primer)

<400> SEQUENCE: 104
gtgcagggtc cgaggt                                                                          16

<210> SEQ ID NO 105
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 105
uagcuuauca gacugauguu ga                                                                   22

<210> SEQ ID NO 106
<211> LENGTH: 31

<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 106
cggtgaggtc tttggttcat aagctatcaa c                          31

<210> SEQ ID NO 107
<211> LENGTH: 22
<212> TYPE: DNA
<213> ORGANISM: Artificial Sequence
<220> FEATURE:
<223> OTHER INFORMATION: Synthetic (miRNA specific PCR primer)

<400> SEQUENCE: 107
cggtagctta tcagactgat gt                                    22

<210> SEQ ID NO 108
<211> LENGTH: 20
<212> TYPE: DNA
<213> ORGANISM: Artificial Sequence
<220> FEATURE:
<223> OTHER INFORMATION: Synthetic (universal PCR primer)

<400> SEQUENCE: 108
cggtgaggtc tttggttcat                                       20

<210> SEQ ID NO 109
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 109
uggaauguaa ggaagugugu gg                                    22

<210> SEQ ID NO 110
<211> LENGTH: 30
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 110
cggtgaggtc tttggttcat attccaccac                            30

<210> SEQ ID NO 111
<211> LENGTH: 19
<212> TYPE: DNA
<213> ORGANISM: Artificial Sequence
<220> FEATURE:
<223> OTHER INFORMATION: Synthetic (miRNA specific PCR primer)

<400> SEQUENCE: 111
cgctggaatg taaggaagt                                        19

<210> SEQ ID NO 112
<211> LENGTH: 20
<212> TYPE: DNA
<213> ORGANISM: Artificial Sequence
<220> FEATURE:
<223> OTHER INFORMATION: Synthetic (universal PCR primer)

```
<400> SEQUENCE: 112
cggtgaggtc tttggttcat                                              20

<210> SEQ ID NO 113
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 113
uagcagcacg uaaauauugg cg                                           22

<210> SEQ ID NO 114
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 114
aagcagcacg uaaauauugg cg                                           22

<210> SEQ ID NO 115
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 115
uugcagcacg uaaauauugg cg                                           22

<210> SEQ ID NO 116
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 116
uaucagcacg uaaauauugg cg                                           22

<210> SEQ ID NO 117
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 117
uagaagcacg uaaauauugg cg                                           22

<210> SEQ ID NO 118
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 118
uagcagcacg uaaauauuug cg                                           22

<210> SEQ ID NO 119
<211> LENGTH: 22
```

```
<212> TYPE: RNA
<213> ORGANISM: Artificial Sequence
<220> FEATURE:
<223> OTHER INFORMATION: Synthetic (microRNA)

<400> SEQUENCE: 119
uagcagcacg uaaauauugc cg                                              22

<210> SEQ ID NO 120
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 120
uagcagcacg uaaauauugg ag                                              22

<210> SEQ ID NO 121
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 121
uagcagcacg uaaauauugg cu                                              22

<210> SEQ ID NO 122
<211> LENGTH: 24
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 122
gtgcagggtc cgaggtgcta cgcc                                            24

<210> SEQ ID NO 123
<211> LENGTH: 22
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 123
gtgcagggtc cgaggtcgcc aa                                              22

<210> SEQ ID NO 124
<211> LENGTH: 20
<212> TYPE: DNA
<213> ORGANISM: Artificial Sequence
<220> FEATURE:
<223> OTHER INFORMATION: Synthetic (miRNA specific PCR primer)

<400> SEQUENCE: 124
cgcgctagca gcacgtaaat                                                 20

<210> SEQ ID NO 125
<211> LENGTH: 16
<212> TYPE: DNA
<213> ORGANISM: Artificial Sequence
<220> FEATURE:
<223> OTHER INFORMATION: Synthetic (universal PCR primer)
```

```
<400> SEQUENCE: 125
gtgcagggtc cgaggt                                                      16

<210> SEQ ID NO 126
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 126
uagcuuauca gacugauguu ga                                               22

<210> SEQ ID NO 127
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 127
augugcgugu gacagcggcu ga                                               22

<210> SEQ ID NO 128
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 128
cagugcgugu gacagcggcu ga                                               22

<210> SEQ ID NO 129
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 129
cuaugcgugu gacagcggcu ga                                               22

<210> SEQ ID NO 130
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 130
cugcgcgugu gacagcggcu ga                                               22

<210> SEQ ID NO 131
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 131
cugugagugu gacagcggcu ga                                               22

<210> SEQ ID NO 132
<211> LENGTH: 22
```

```
<212> TYPE: RNA
<213> ORGANISM: Artificial Sequence
<220> FEATURE:
<223> OTHER INFORMATION: Synthetic (microRNA)

<400> SEQUENCE: 132
cugugcgugu gacagcgguu ga                                          22

<210> SEQ ID NO 133
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 133
cugugcgugu gacagcggcg ga                                          22

<210> SEQ ID NO 134
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 134
cugugcgugu gacagcggcu aa                                          22

<210> SEQ ID NO 135
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 135
cugugcgugu gacagcggcu gg                                          22

<210> SEQ ID NO 136
<211> LENGTH: 34
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 136
ccggtgaggt ctttggttca tacgcacagt cagc                             34

<210> SEQ ID NO 137
<211> LENGTH: 26
<212> TYPE: DNA
<213> ORGANISM: Artificial Sequence
<220> FEATURE:
<223> OTHER INFORMATION: Synthetic (3' priming reverse transcription
      primer)

<400> SEQUENCE: 137
cggtgaggtc tttggttcat tcagcc                                      26

<210> SEQ ID NO 138
<211> LENGTH: 16
<212> TYPE: DNA
<213> ORGANISM: Artificial Sequence
<220> FEATURE:
<223> OTHER INFORMATION: Synthetic (miRNA specific PCR primer)
```

```
<400> SEQUENCE: 138
ctgtgcgtgt gacagc                                                          16

<210> SEQ ID NO 139
<211> LENGTH: 20
<212> TYPE: DNA
<213> ORGANISM: Artificial Sequence
<220> FEATURE:
<223> OTHER INFORMATION: Synthetic (universal PCR primer)

<400> SEQUENCE: 139
cggtgaggtc tttggttcat                                                      20

<210> SEQ ID NO 140
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 140
ugagguagua gguuguauag uu                                                   22

<210> SEQ ID NO 141
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 141
ugagguagua gguugugugg uu                                                   22

<210> SEQ ID NO 142
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 142
ugagguagua gguuguaugg uu                                                   22

<210> SEQ ID NO 143
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 143
agagguagua gguugcauag uu                                                   22

<210> SEQ ID NO 144
<211> LENGTH: 22
<212> TYPE: RNA
<213> ORGANISM: Artificial Sequence
<220> FEATURE:
<223> OTHER INFORMATION: Synthetic (microRNA)

<400> SEQUENCE: 144
ugagguagga gguuguauag uu                                                   22

<210> SEQ ID NO 145
<211> LENGTH: 26
```

<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 145
gtgcagggtc cgaggtacct caaact                                     26

<210> SEQ ID NO 146
<211> LENGTH: 26
<212> TYPE: DNA
<213> ORGANISM: Artificial Sequence
<220> FEATURE:
<223> OTHER INFORMATION: Sytnthetic (Dual hybridization reverse
      transcription primer)

<400> SEQUENCE: 146
gtgcagggtc cgaggtacct caaacc                                     26

<210> SEQ ID NO 147
<211> LENGTH: 26
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 147
gtgcagggtc cgaggtacct caaacc                                     26

<210> SEQ ID NO 148
<211> LENGTH: 26
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 148
gtgcagggtc cgaggtacct ctaact                                     26

<210> SEQ ID NO 149
<211> LENGTH: 26
<212> TYPE: DNA
<213> ORGANISM: Artificial Sequence
<220> FEATURE:
<223> OTHER INFORMATION: Synthetic (Dual hybridization reverse
      transcription primer)

<400> SEQUENCE: 149
gtgcagggtc cgaggtacct caaact                                     26

<210> SEQ ID NO 150
<211> LENGTH: 22
<212> TYPE: DNA
<213> ORGANISM: Artificial Sequence
<220> FEATURE:
<223> OTHER INFORMATION: Synthetic (miRNA specific PCR primer)

<400> SEQUENCE: 150
gccgctgagg tagtaggttg ta                                         22

<210> SEQ ID NO 151
<211> LENGTH: 20
<212> TYPE: DNA
<213> ORGANISM: Artificial Sequence

```
<220> FEATURE:
<223> OTHER INFORMATION: Synthetic (miRNA specific PCR primer)

<400> SEQUENCE: 151
cgctgaggta gtaggttgtg                                               20

<210> SEQ ID NO 152
<211> LENGTH: 22
<212> TYPE: DNA
<213> ORGANISM: Artificial Sequence
<220> FEATURE:
<223> OTHER INFORMATION: Synthetic (miRNA specific PCR primer)

<400> SEQUENCE: 152
gccgctgagg tagtaggttg ta                                            22

<210> SEQ ID NO 153
<211> LENGTH: 21
<212> TYPE: DNA
<213> ORGANISM: Artificial Sequence
<220> FEATURE:
<223> OTHER INFORMATION: Synthetic (miRNA specific PCR primer)

<400> SEQUENCE: 153
gccgcagagg tagtaggttg c                                             21

<210> SEQ ID NO 154
<211> LENGTH: 18
<212> TYPE: DNA
<213> ORGANISM: Artificial Sequence
<220> FEATURE:
<223> OTHER INFORMATION: Synthetic (miRNA specific PCR primer)

<400> SEQUENCE: 154
tgccggtgag gtaggagg                                                 18
```